(12) United States Patent
Khan et al.

(10) Patent No.: US 9,434,753 B2
(45) Date of Patent: Sep. 6, 2016

(54) MODIFIED CREATINE COMPOUNDS

(71) Applicant: Gencia Corporation, Charlottesville, VA (US)

(72) Inventors: Shaharyar M. Khan, Charlottesville, VA (US); Robert Gadwood, Portage, MI (US); Arthur Glenn Romero, Chesterfield, MO (US)

(73) Assignee: Gencia Corporation, Charlottesville, VA (US)

( * ) Notice: Subject to any disclaimer, the term of this patent is extended or adjusted under 35 U.S.C. 154(b) by 0 days.

(21) Appl. No.: 14/345,503

(22) PCT Filed: Sep. 18, 2012

(86) PCT No.: PCT/US2012/055887
§ 371 (c)(1),
(2) Date: Mar. 18, 2014

(87) PCT Pub. No.: WO2013/043580
PCT Pub. Date: Mar. 28, 2013

(65) Prior Publication Data
US 2015/0005258 A1     Jan. 1, 2015

Related U.S. Application Data

(60) Provisional application No. 61/536,280, filed on Sep. 19, 2011.

(51) Int. Cl.
| | | |
|---|---|---|
| C07F 9/54 | (2006.01) | |
| C07F 9/655 | (2006.01) | |
| C07F 9/6506 | (2006.01) | |
| C07F 9/22 | (2006.01) | |

(52) U.S. Cl.
CPC .............. *C07F 9/5456* (2013.01); *C07F 9/22* (2013.01); *C07F 9/5442* (2013.01); *C07F 9/6552* (2013.01); *C07F 9/65061* (2013.01)

(58) Field of Classification Search
None
See application file for complete search history.

(56) References Cited

U.S. PATENT DOCUMENTS

| | | |
|---|---|---|
| 6,242,491 B1 | 6/2001 | Kaddurah-Daouk |
| 6,290,973 B1 | 9/2001 | Hawkins et al. |
| 6,534,535 B1 | 3/2003 | Zhu et al. |
| 6,825,191 B2 | 11/2004 | Nakagawa et al. |
| 7,148,063 B2 | 12/2006 | Shirahase et al. |
| 7,915,230 B2 | 3/2011 | Jessee et al. |
| 2004/0006242 A1 | 1/2004 | Hawkins et al. |
| 2007/0066572 A1 | 3/2007 | Balaraman et al. |
| 2007/0191314 A1 | 8/2007 | Klucker et al. |
| 2010/0179106 A1* | 7/2010 | Khan ........................... 514/77 |
| 2011/0212975 A1 | 9/2011 | Kao et al. |
| 2012/0052574 A1 | 3/2012 | Jessee et al. |

FOREIGN PATENT DOCUMENTS

| | | |
|---|---|---|
| EP | 1109805 B1 | 12/2003 |
| WO | 96/14063 | 5/1996 |
| WO | 99/51097 | 10/1999 |
| WO | 00/11952 A1 | 3/2000 |
| WO | 01/00671 | 1/2001 |
| WO | 2003/080603 A1 | 10/2003 |
| WO | 2004/070054 | 8/2004 |
| WO | 2005/019232 | 3/2005 |
| WO | 2006/005759 | 1/2006 |
| WO | 2007/130073 A2 | 11/2007 |

(Continued)

OTHER PUBLICATIONS

Parikh et al., A Modern Approach to the Treatment of Mitochondrial Disease. Current Treatment Options in Neurology, 2009, 11, 414-430.*

(Continued)

*Primary Examiner* — Rebecca Anderson
*Assistant Examiner* — Po-Chih Chen
(74) *Attorney, Agent, or Firm* — Honigman Miller Shwartz and Cohn LLP; Lucy X. Yang; Jonathan P. O'Brien

(57) ABSTRACT

The invention discloses creatine derivatives that are represented by Formula (I), Formula (II), and Formula (III); wherein Z is a functional group; Y is a mitochondrial targeting agent, a cationic ammonium group, or a polypeptide containing at least one positively charged amino acid residue; each $R_1$ is independently hydrogen, alkyl, or a phosphate group; $R_2$ a linker; $R_3$ is a spacer group; $R_4$ is hydrogen, alkyl, aryl, or heterocyclic; or $R_4$ and $R_1$, or $R_4$ and $R_3$, together with the nitrogen atoms to which they are attached form a heterocyclic ring, and W is hydrogen or alkyl.

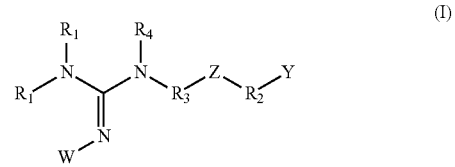

(I)

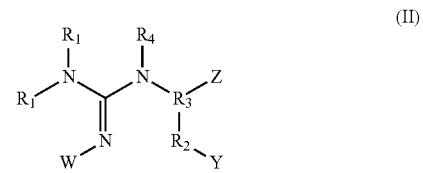

(II)

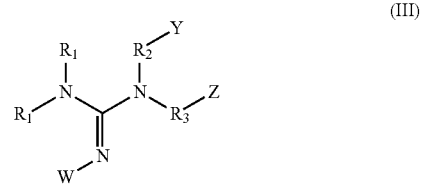

(III)

18 Claims, 4 Drawing Sheets

(56) References Cited

FOREIGN PATENT DOCUMENTS

| WO | 2009/033130 | A1 | 3/2009 |
|---|---|---|---|
| WO | 2009/105712 | | 8/2009 |
| WO | 2009/111846 | A1 | 9/2009 |
| WO | 2011/011366 | | 1/2011 |
| WO | 2011/082328 | | 7/2011 |
| WO | 2011/147199 | A1 | 12/2011 |

OTHER PUBLICATIONS

Shafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Dong, Lan-Feng et al. J. Biol Chem. Feb. 4, 2011; 286(5): pp. 3717-3728.

Tse, Brian N., et al. Translation of DNA into a Library of 13,000 Synthetic Small-Molecule Macrocycles Suitable for In Vitro Selection. J Am Chem Society. Nov. 19, 2008; 130(46) pp. 15611-15626.

Albrieux et al. Conformation of Polyalanine and Polyglycine Dications in the Gas Phase: Insight from Ion Mobility Spectrometry and Replica-Exchange Molecular Dynamics. Journal of Physcial Chemistry A. vol. 114, No. 25, pp. 6888-6896. Jun. 10, 2010.

Chaturvedi et al. Mitochondrial Approaches for Neuroprotection. Annals of the New York Academy of Sciences. vol. 1147, pp. 395-412. Dec. 2008.

Couture et al. Specificity and mechanism of JMJD2A, a trimethyllysine-specific histone demethylase. Nature Structural and Molecular Biology. vol. 14, No. 8, pp. 689-695. Jun. 24, 2007.

Neff et al. Through-speace and through-bond electron transfer within positively charged peptimes in the gas phase. International Journal of Mass Spectrometry. vol. 276, pp. 91-101. 2007.

Pitteri et al. Electron-Transfer Ion/Ion Reactions of Doubly Protonated Peptides: Effect of Elevated Bath Gas Temperature. Analytical Chemistry. vol. 77, No. 17, pp. 5662-5669. Sep. 1, 2005.

Popa et al. Capillary electrophoresis of cationic random coil peptide standards: Effect of anionic ion-pairing reagents and comparison with reversed-phase chromatography. Electrophoresis. vol. 25, pp. 1219-1229. 2004.

Stewart et al. Design, Synthesis, and Characterization of a Novel Class of Mitochondrial Delivery Vectors: Mitochondria-penetrating Peptimes. A thesis submitted in conformity with requirements for the degree of Doctor of Philosophy Department of Biochemistry, Faculty of Medicine University of Toronto. Feb. 23, 2011.

Xia et al. Effects of Cation Charge-Site Identity and Position on Electron-Transfer Dissociation of Polypeptide Cations. Journal of the American Society. vol. 129, No. 40, pp. 12232-12243. May 22, 2007.

Yousif et al. Mitochondria-penetrating Peptides: Characterization and Cargo Delivery. A thesis submitted in conformity with the requirements for the degree of Master Science Graduate Department of Biochemistry University of Toronto. Feb. 17, 2010.

* cited by examiner

```
                        SEQUENCE LISTING

<160> NUMBER OF SEQ ID NOS: 7

<210> SEQ ID NO 1
<211> LENGTH: 11
<212> TYPE: PRT
<213> ORGANISM: Human immunodeficiency virus

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Human immunodeficiency virus

<400> SEQUENCE: 2

Arg Lys Lys Arg Arg Gln Arg Arg Arg
1               5

<210> SEQ ID NO 3
<211> LENGTH: 0
<212> TYPE: PRT
<213> ORGANISM: Artificial Sequence
<220> FEATURE:
<223> OTHER INFORMATION: synthetically generated peptide

<400> SEQUENCE: 3

000

<210> SEQ ID NO 4
<211> LENGTH: 12
<212> TYPE: PRT
<213> ORGANISM: Artificial Sequence
<220> FEATURE:
<223> OTHER INFORMATION: Synthetically generated peptide

<400> SEQUENCE: 4

Arg Arg Gln Arg Arg Thr Ser Lys Leu Met Lys Arg
1               5                   10

<210> SEQ ID NO 5
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 5

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 6
<211> LENGTH: 29
<212> TYPE: PRT
<213> ORGANISM: Artificial Sequence
```

```
<220> FEATURE:
<223> OTHER INFORMATION: Synthetically generated peptide

<400> SEQUENCE: 6

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 7
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 7

Arg Gln Ile Lys Ile Trp Phe Gln Asn Arg Arg Met Lys Trp Lys Lys
1               5                   10                  15
```

MODIFIED CREATINE COMPOUNDS

CROSS REFERENCE TO RELATED APPLICATION

This U.S. patent application claims benefit of PCT Application No. PCT/US2012/055887, filed on Sep. 18, 2012, which claims the benefit of U.S. provisional Application No. 61/536,280 filed on Sep. 19, 2011. The entire contents of which are incorporated by reference in their entireties.

SEQUENCE LISTING STATEMENT

This application incorporates by reference in its entirety the Sequence Listing entitled "331582_ST25.txt" (1.91 kilobytes), which was created on Sep. 18, 2012, and filed electronically herewith.

FIELD OF THE INVENTION

The present invention relates to creatine derivatives, including creatine derivatives functionalized with one more mitochondrial targeting agents, and methods of making and using creatine derivatives.

BACKGROUND OF THE INVENTION

Creatine (Cr), or 2-(carbamimidoyl-methyl-amino) acetic acid, is a naturally occurring nitrogenous organic acid that is synthesized in the liver of vertebrates and helps to supply energy to muscle and nerve cells. Creatine is synthesized from the amino acids arginine, methionine, and glycine through a two-step enzymatic process involving GAMT (guanidinoacetate N-methyltransferase, also known as glycine amidinotransferase) by methylation of guanidoacetate using S-adenosyl-L-methionine (SAM) as the methyl donor. Guanidoacetate itself is formed in the kidneys from the amino acids arginine and glycine. Once made in the liver or acquired through digestion, creatine is stored in cells including muscle and brain cells.

The enzyme creatine (phospho)kinase (CPK or CK), catalyzes the transfer of the phosphate from ATP to the guanidinium of creatine, forming creatine phosphate (PCr). The reaction is reversible, such that when energy demand is high (e.g., during muscle exertion or brain activity), CPK can dephosphorylate creatine phosphate and transfer the phosphate back to ADP forming ATP. This enables creatine to act as an energy storage molecule where phosphate can be stored independently of ATP.

Perturbed mitochondrial function can lead to ATP depletion, resulting in significant physiological problems. One potential method of addressing ATP depletion is to increase phosphocreatine (PCr) stores, for example by administering creatine which can be phosphorylated by CPK. Several forms of CPK exist but the most ubiquitous form of the enzyme resides in the mitochondrion, where it produces phosphocreatine from mitochondrially-generated ATP and creatine from the cytosol. However, creatine transport from the mitochondrion is an energy requiring process. Accordingly, a need remains for creatine analogs targeted to the mitochondrion to circumvent the energy loss associated with endogenous creatine transport and to provide creatine at the subcellular location of creatine action.

SUMMARY OF THE INVENTION

The present invention provides a compound of Formula I $$\underset{W}{\overset{R_1}{\underset{R_1}{N}}}\text{—}\underset{N}{\overset{R_4}{N}}\text{—}\underset{R_3}{N}\text{—}Z\text{—}R_2\text{—}Y \quad \text{I}$$

or a pharmaceutically acceptable salt thereof wherein

Z is —C(=O)NR$_5$—, —OC(=O)NR$_5$—, —NR$_5$C(=O)O—, —NR$_5$C(=O)NR$_5$—, —SO$_2$NR$_5$—, —NR$_5$SO$_2$—, —O—, —S—, or —S—S—; wherein each R$_5$ is independently hydrogen, alkyl, aryl, or heterocyclic;

Y is a cationic phosphonium group, or a polypeptide containing at least one positively charged amino acid residue;

each R$_1$ is independently hydrogen, alkyl, or a phosphate group;

R$_2$ is absent, alkyl, cycloalkyl, heterocycloalkyl, alkylaryl, alkylarylalkyl, or aryl, R$_3$ is alkyl, cycloalkyl, alkylcycloalkyl, heterocycloalkyl, alkylheterocycloalkyl, alkylaryl, or alkylarylalkyl;

R$_4$ is hydrogen, alkyl, or aryl; or

R$_4$ and a R$_1$ group together with the nitrogen atoms to which they are attached form a heterocyclic ring containing at least five atoms; or R$_4$ and R$_3$ together with the nitrogen atom to which they are attached form a heterocyclic ring containing at least five atoms;

at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; or at each occurrence, an aryl is optionally substituted with 1-5 substituents independently selected from halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and nitrile; and W is hydrogen or alkyl;

with the provisos that when Y is a cationic phosphonium group Z and Y are not substituted on the same R$_2$ carbon; and that Z and the —NR$_4$— moiety are not substituted on the same R$_3$ carbon.

The present invention further provides a compound of Formula II or Formula III $$\underset{W}{\overset{R_1}{\underset{R_1}{N}}}\text{—}\underset{N}{\overset{R_4}{N}}\text{—}\underset{R_3}{\overset{Z}{\underset{R_2}{|}}}\text{—}Y \quad \text{II}$$

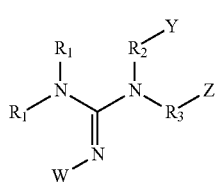

or a pharmaceutically acceptable salt thereof wherein:

Z is a functional group such as —C(=O)NR$_5$R$_5$, —NR$_5$C(=O)OR$_5$, —NR$_5$C(=O)NR$_5$R$_5$, —O(C=O)NR$_5$R$_5$, —SO$_2$NR$_5$R$_5$, —NR$_5$SO$_2$R$_5$, —OR$_5$, —SR$_5$, —S—SR$_5$, —CR$_5$OH, or —CR$_5$SH$_2$, with the proviso that Z and —NR$_4$— moiety are not substituted on the same R$_3$ carbon when Z is —NR$_5$C(=O)OR$_5$, —NR$_5$C(=O)NR$_5$R$_5$, —O(C=O)NR$_5$R$_5$, —SO$_2$NR$_5$R$_5$, —NR$_5$SO$_2$R$_5$, —OR$_5$, —SR$_5$, or —S—SR$_5$; and wherein each R$_5$ is independently hydrogen, alkyl, aryl, or heterocyclic;

Y is a mitochondrial targeting agent such as cationic phosphonium group, a cationic ammonium group, or a polypeptide containing at least one positively charged amino acid residue;

each R$_1$ is independently hydrogen, alkyl, or a phosphate group;

R$_2$ is absent, or a linker selected from the list comprising alkyl, cycloalkyl, heterocycloalkyl, alkylaryl, alkylarylalkyl, or aryl, with the proviso that when Y is a cationic phosphonium group, the guanidine nitrogen and Y are not substituted on the same R$_2$ carbon;

R$_3$ is a spacer group selected from the list comprising alkyl, cycloalkyl, alkylcycloalkyl, heterocycloalkyl, alkylheterocycloalkyl, alkylaryl, or alkylarylalkyl, with the proviso that Z and the guanidine nitrogen are not substituted on the same R$_3$ carbon;

R$_4$ is hydrogen, alkyl, aryl, or heterocyclic; or

R$_4$ and a R$_1$ group together with the nitrogen atoms to which they are attached form a heterocyclic ring containing at least five atoms; or R$_4$ and R$_3$ together with the nitrogen atom to which they are attached form a heterocyclic ring containing at least five atoms; at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl.

at each occurrence, an aryl is optionally substituted with 1-5 substituents independently selected from halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and nitrile; and W is hydrogen or alkyl.

The present invention further provides:

a pharmaceutical composition comprising a compound of Formula I, II or III;

a method of enhancing mitochondrial function in a patient in need thereof, comprising administering the pharmaceutical composition of Formula I, II or III in an amount effective to enhance mitochondrial function in a patient;

a method of increasing ATP production in mitochondria of a patient, comprising administering the pharmaceutical composition of Formula I, II or III in an amount effective to increase ATP production in the mitochondria of the subject; and a method of treating a mitochondrially-related disorder in a patient in need thereof, comprising administering the pharmaceutical composition of Formula I, II or III in an amount effective to treat one or more symptoms of the mitochondrially-related disorder in the patient.

The present invention further provides methods of making and using the creatine compounds of the present invention.

DETAILED DESCRIPTION OF THE INVENTION

Figure 1:
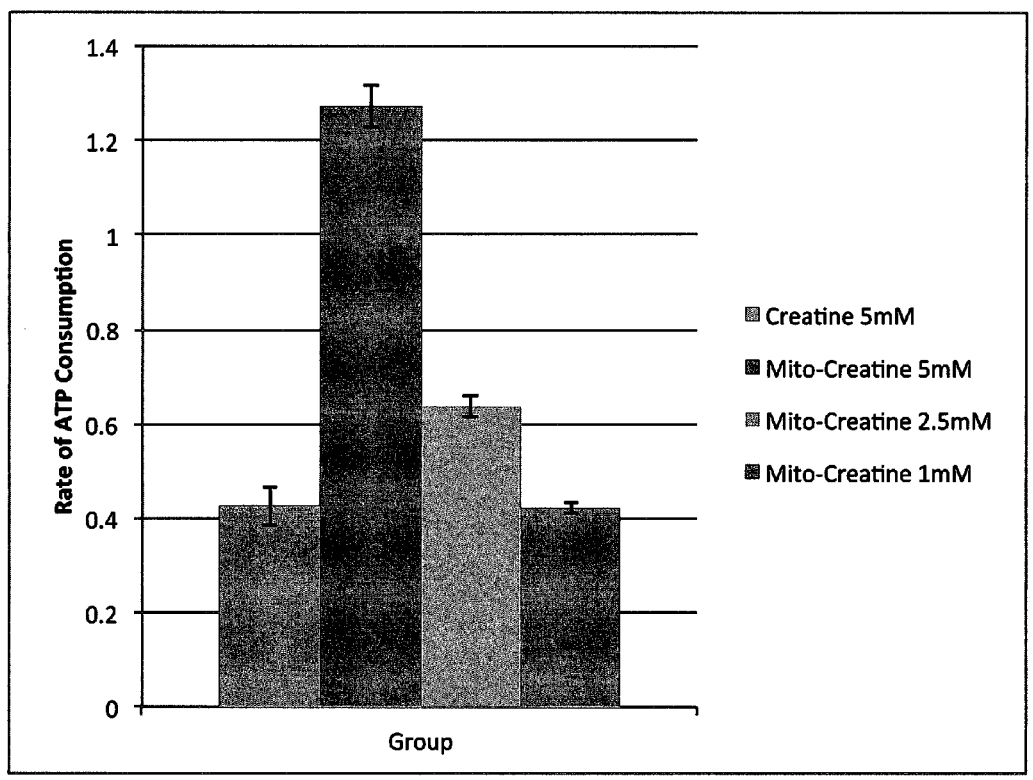
FIG. 1 depicts a bar graph plotting the rate of ATP consumption upon addition of creatine (5 mM) and creatine compound 1 (5 mM, 2.5 mM, and 1 mM) to a solution of ATP and recombinant CPK. Addition of creatine caused an increase in ATP hydrolysis/consumption. Equimolar concentration of Mito-Creatine (compound 1) had a significantly higher rate of ATP hydrolysis/consumption than creatine, demonstrating improved activity on recombinant CPK.

Modified creatine compounds containing a creatine subunit operably linked to one or more agents, such as a mitochondrial targeting agent, are provided. Exemplary modified creatine compounds are represented by the general formulae shown below:

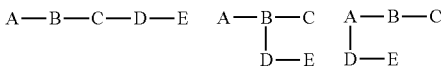

wherein A, B, and C, in combination, represent a creatine subunit, with A representing a guanidine or modified guanidine moiety, B representing a spacer group, and C representing a functional group; D represents an optional linker; and E represents an agent.

As illustrated by the general formulae above, the agent E is typically linked to the creatine subunit A-B-C by way of a linker D. In some cases, the linker D can be absent, and the agent E can be directly connected to the creatine subunit A-B-C. The agent E, optionally by means of a linker D, can be connected to any portion of the creatine subunit, that is, to the guanidine moiety A, the spacer group B, or the functional group C.

In one aspect, the modified creatine compounds are represented by Formula I

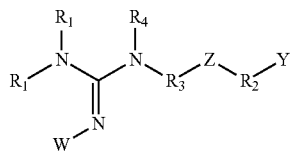

or a pharmaceutically acceptable salt thereof wherein Z is —C(=O)NR$_5$—, —OC(=O)NR$_5$—, —NR$_5$C(=O)O—, —NR$_5$C(=O)NR$_5$—, —SO$_2$NR$_5$—, —NR$_5$SO$_2$—, —O—, —S—, or —S—S—, wherein each R$_5$ is independently hydrogen, alkyl, aryl, or heterocyclic; Y is a cationic phosphonium group, a cationic ammonium group, or a polypeptide containing at least one positively charged amino acid residue; each R$_1$ is independently hydrogen, alkyl, or a phosphate group; R$_2$ is absent, alkyl, cycloalkyl, heterocycloalkyl, alkylaryl, alkylarylalkyl, or aryl, with the proviso that when Y is a cationic phosphonium group Z and Y are not substituted on the same R$_2$ carbon; R$_3$ is alkyl, cycloalkyl, alkylcycloalkyl, heterocycloalkyl, alkylheterocycloalkyl, alkylaryl, or alkylarylalkyl, with the proviso that Z and —NR$_4$— moiety are not substituted on the same R$_3$ carbon; R$_4$ is hydrogen, alkyl, or aryl; or R$_4$ and a R$_1$ group together with the nitrogen atoms to which they are attached form a heterocyclic ring containing at least five atoms; or R$_4$ and R$_3$ together with the nitrogen atom to which they are attached form a heterocyclic ring containing at least five atoms; at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; or at each occurrence, an aryl is optionally substituted with 1-5 substituents independently selected from halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and nitrile; and W is hydrogen or alkyl.

Specifically, the present invention provides a compound of Formula I wherein Z is —C(=O)NR$_5$—, —OC(=O)NR$_5$—, —NR$_5$C(=O)O—, or —NR$_5$C(=O)NR$_5$—; wherein each R$_5$ is independently hydrogen, or C$_{1-6}$ alkyl; Y is a cationic phosphonium group; each R$_1$ is independently hydrogen, alkyl, or a phosphate group; R$_2$ is alkyl, cycloalkyl, heterocycloalkyl, or alkylaryl; R$_3$ is alkyl, cycloalkyl, alkylcycloalkyl, heterocycloalkyl, alkylheterocycloalkyl, or alkylaryl; R$_4$ is hydrogen, or C$_{1-6}$ alkyl; and W is hydrogen.

Specifically, the present invention provides a compound of Formula I wherein Z is —C(=O)NR$_5$—, wherein R$_5$ is hydrogen, or C$_{1-6}$ alkyl; Y is —P$^+$(R')$_3$X$^-$, wherein R' is alkyl or aryl; and X$^-$ is an anion; each R$_1$ is independently hydrogen, or —PO$_3$$^{2-}$M, wherein M is a pharmaceutically acceptable cation, including metal cations, having one or two positive charges such as M$^+$, or M$^{2+}$; R$_2$ is straight or branched C$_{1-8}$ alkyl; R$_3$ is alkyl, cycloalkyl, alkylcycloalkyl, heterocycloalkyl, or alkylheterocycloalkyl, wherein alkyl is straight or branched C$_{1-12}$ alkyl, cycloalkyl comprises 3-8 carbon atoms, heterocycloalkyl is a cyclic ring of 5-10 atoms having at least one hetero atom selected from sulfur, non-peroxide oxygen, or nitrogen; R$_4$ is hydrogen or C$_{1-4}$ alkyl; and W is hydrogen.

Specifically, the present invention provides a compound of Formula I wherein Z is —C(=O)NH, Y is —P$^+$(Phenyl)$_3$X$^-$, wherein X$^-$ is chloride, or trifluoroacetate; R$_1$ is hydrogen; R$_2$ is C$_{1-8}$alkyl; R$_3$ is C$_{1-6}$ alkyl, C$_{1-6}$alkylcycloalkyl wherein cycloalkyl comprising 3-6 carbon atoms, or C$_{1-6}$alkylheterocycloalkyl wherein heterocycloalkyl is a cyclic ring of 5-6 atoms having a nitrogen atom; and R$_4$ is methyl.

Specifically, a compound of Formula I wherein Z is —C(=O)NR$_5$—, and R$_5$ is hydrogen, or C$_{1-6}$ alkyl.

Specifically, a compound of Formula I wherein Z is —C(=O)NH—.

Specifically, a compound of Formula I wherein a cationic phosphonium group is selected from —P$^+$(R')$_3$X$^-$, wherein R' is alkyl or aryl; and X$^-$ is an anion.

Specifically, a compound of Formula I wherein R' is phenyl; and X$^-$ is chloride, or trifluoroacetate.

Specifically, a compound of Formula I wherein at least one R$_1$ is hydrogen.

Specifically, a compound of Formula I wherein both R$_1$ are hydrogen.

Specifically, a compound of Formula I wherein one R$_1$ is hydrogen, the other R$_1$ is —PO$_3$$^{2-}$M;

Specifically, a compound of Formula I wherein R$_2$ is straight or branched C$_{1-20}$ alkyl.

Specifically, a compound of Formula I wherein R$_2$ is C$_{3-8}$ alkyl.

Specifically, a compound of Formula I wherein R$_3$ is alkyl, cycloalkyl, alkylcycloalkyl, heterocycloalkyl, or alkylheterocycloalkyl, wherein alkyl is straight or branched.

Specifically, a compound of Formula I wherein R$_3$ is C$_{1-8}$ alkyl.

Specifically, a compound of Formula I wherein R$_3$ is C$_{1-6}$ alkylcycloalkyl wherein cycloalkyl comprises 3-8 carbon atoms.

Specifically, a compound of Formula I wherein R$_3$ is C$_{1-6}$ alkylcycloalkyl wherein cycloalkyl comprising 3-6 carbon atoms.

Specifically, a compound of Formula I wherein R$_3$ is C$_{1-6}$ alkylheterocycloalkyl wherein heterocycloalkyl is a cyclic ring of 3-10 atoms having at least one hetero atom selected from sulfur, non-peroxide oxygen, or nitrogen.

Specifically, a compound of Formula I wherein R$_3$ is C$_{1-6}$ alkylheterocycloalkyl wherein heterocycloalkyl is a cyclic ring of 5-6 atoms.

Specifically, a compound of Formula I wherein R$_4$ is hydrogen or C$_{1-4}$ alkyl.

Specifically, a compound of Formula I wherein R$_4$ is methyl.

The present invention further provides a compound of Formula I which is a pharmaceutically acceptable salt of Formula IX

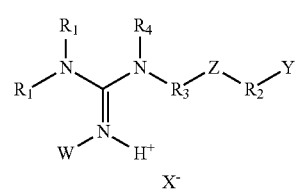

wherein X$^-$ is an anion.

The present invention further provides a compound of Formula II or III

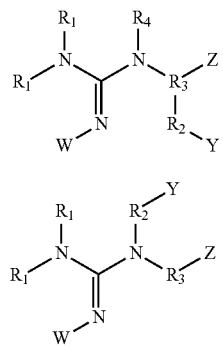

or a pharmaceutically acceptable salt thereof wherein Z is a functional group; Y is a mitochondrial targeting agent, a cationic ammonium group, or a polypeptide containing at least one positively charged amino acid residue; each $R_1$ is independently hydrogen, alkyl, or a phosphate group; $R_2$ is absent, or a linker; $R_3$ is a spacer group; $R_4$ is hydrogen, alkyl, aryl, or heterocyclic; or $R_4$ and a $R_1$ group together with the nitrogen atoms to which they are attached form a heterocyclic ring containing at least five atoms; or $R_4$ and $R_3$ together with the nitrogen atom to which they are attached form a heterocyclic ring containing at least five atoms; at each occurrence, an alkyl is optionally substituted with 1-3 substituents independently selected from halo, haloalkyl, hydroxyl, amino, thio, ether, ester, carboxy, oxo, aldehyde, cycloalkyl, nitrile, urea, amide, carbamate and aryl; at each occurrence, an aryl is optionally substituted with 1-5 substituents independently selected from halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and nitrile; and W is hydrogen or alkyl; with the provisos that Z and —$NR_4$-moiety are not substituted on the same $R_3$ carbon when Z is —$NR_5C(=O)OR_5$, —$NR_5C(=O)NR_5R_5$, —$O(C=O)NR_5R_5$, —$SO_2NR_5R_5$, —$NR_5SO_2R_5$, —$OR_5$, —$SR_5$, or —S—$SR_5$; and that when Y is a cationic phosphonium group, nitrogen and Y are not substituted on the same $R_2$ carbon.

Specifically, a compound of Formula II or III wherein Z is —C(=O)N($R_5$)$_2$, —C(=O)N($R_5$)$_2$, —$NR_5C(=O)O$ ($R_5$), —$NR_5C(=O)N(R_5)_2$, —$SO_2N(R_5)_2$, —$NR_5SO_2R_5$, —O($R_5$), —S($R_5$), —S—S($R_5$), —C($R_5$)$_2$OH, or —C($R_5$)$_2$SH; wherein $R_5$ is hydrogen, alkyl, aryl, or heterocyclic; Y is a cationic phosphonium group, a catalytic ammonium group, or a polypeptide containing at least one positively charged amino acid residue; $R_1$ is independently hydrogen, alkyl, or a phosphate group; $R_2$ is absent, alkyl, cycloalkyl, heterocycloalkyl, alkylaryl, alkylarylalkyl, or aryl; $R_3$ is alkyl, cycloalkyl, alkylcycloalkyl, heterocycloalkyl, alkylheterocycloalkyl, alkylaryl, or alkylarylalkyl; $R_4$ is hydrogen, alkyl, or aryl; and W is hydrogen or alkyl; with the proviso that when Y is a cationic phosphonium group Z and Y are not substituted on the same $R_2$ carbon; and with the proviso that Z and the guanidine nitrogen are not substituted on the same $R_3$ carbon.

Specifically, a compound of Formula II or III is wherein Z is —C(=O)N($R_5$)$_2$, —C(=O)N($R_5$)$_2$, —$NR_7C(=O)O$ ($R_5$), or —$NR_5C(=O)N(R_5)_2$, —$SO_2N(R_5)_2$, wherein each $R_5$ is independently hydrogen, or $C_{1-6}$ alkyl; Y is a cationic phosphonium group; each $R_1$ is independently hydrogen, alkyl, or a phosphate group; $R_2$ is alkyl, cycloalkyl, heterocycloalkyl, or alkylaryl; $R_3$ is alkyl, cycloalkyl, alkylcycloalkyl, heterocycloalkyl, alkylheterocycloalkyl, or alkylaryl; and $R_4$ is hydrogen, or $C_{1-6}$alkyl; and W is hydrogen; with the proviso that when Y is a cationic phosphonium group Z and Y are not substituted on the same $R_2$ carbon; and with the proviso that Z and the guanidine nitrogen are not substituted on the same $R_3$ carbon.

Specifically, a compound of Formula II, or III is a pharmaceutically acceptable salt of Formula IIX, or IIIX

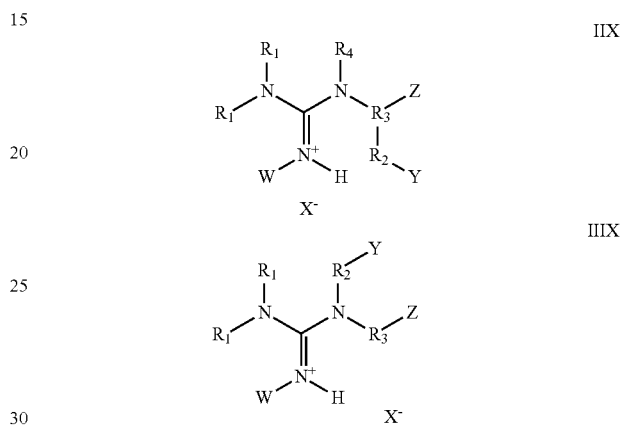

wherein $X^-$ is an anion.

An in vitro assay for determining the activity of the modified creatine compounds on recombinant CPK is described herein, as well as assays for measuring the ability of modified creatine compounds to increase the oxygen consumption rate (OCR) and Complex I (CI) activity in cells.

In some aspects, pharmaceutical compositions containing one or more creatine compounds and one or more pharmaceutically acceptable excipients and/or carrier are used to modify mitochondrial function or treat one or more symptoms of a mitochondrial disorder are also described. The compounds described herein can be formulated for a variety of routes of administration, including enteral (e.g., oral), parenteral (e.g., intravenous), or topical (e.g., transdermal).

In some aspects, pharmaceutical compositions may be administered to treat a variety of diseases or disorders of the mitochondria. Exemplary diseases and disorders include, but are not limited to, mitochondrial myopathies (e.g., Kearns-Sayre syndrome, Leigh's syndrome, mitochondrial DNA depletion syndrome (MDS), mitochondrial encephalomyopathy, lactic acidosis, and stroke-like episodes (MELAS)), myoclonus epilepsy with ragged red fibers (MERRF), mitochondrial neurogastrointestinal encephalomyopathy (MNGIE), neuropathy, ataxia, retinitis pigmentosa (NARP), and progressive external ophthalmoplegia (PEO).

Additionally, in another aspect, the compounds disclosed herein can be used to treat one or more symptoms of creatine deficiency syndromes, arthritis, congestive heart failure, disuse atrophy, gyrate atrophy, Huntington's disease, Parkinson's disease, and McArdles disease.

In other aspects, processes for synthesizing the compounds of Formulae I, II, and III are disclosed.

In describing and claiming the disclosed subject matter, the following terminology will be used in accordance with the definitions set forth below.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The carbon atom content of various hydrocarbon-containing moieties is indicated by a prefix designating the minimum and maximum number of carbon atoms in the moiety, i.e., the prefix $C_{i-j}$ or $C_i$-$C_j$ indicates a moiety of the integer "i" to the integer "j" carbon atoms, inclusive. Thus, for example, $C_{1-4}$ alkyl refers to alkyl of one to four carbon atoms, inclusive.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more particularly 20 or fewer carbon atoms, more particularly 12 or fewer carbon atoms, and most particularly 8 or fewer carbon atoms. Likewise, some cycloalkyls have from 3-10 carbon atoms in their ring structure, and more particularly have 5, 6 or 7 carbons in the ring structure. The ranges provided above are inclusive of all values between the minimum value and the maximum value.

The alkyl groups may also be substituted with one or more groups including, but not limited to, halogen, hydroxy, amino, thio, ether, ester, carboxy, oxo, and aldehyde groups. The alkyl groups may also contain one or more heteroatoms within the carbon backbone. Particularly the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and particularly from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, particularly 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "Pharmaceutically acceptable salt", as used herein, refers to derivatives of the compounds defined herein, wherein the parent compound is modified by making acid or base salts thereof, and/or a phosphonium or ammonium cation is present. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable acid or base salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are examples. When selected to be present, the anion counter-ion for the phosphonium ion may be prepared by a variety of methods, including the direct result of the quaternization of the phosphine and the application of ion-exchange to replace one counter-ion for another. Lists of suitable salts and counter-ions are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. Pharmaceutically acceptable carriers and/or excipients include those include compounds or materials generally recognized as safe (GRAS) by the U.S. Food and Drug Administration.

The term "host," as used herein, refers to a multicellular organism having mitochondria including but not limited to mammals such as primates, humans, dogs, cats, cows, pigs, sheep, and the like.

The term "mitochondrial metabolite," as used herein, refers to an organic compound that is a starting material in, an intermediate in, or an end product of metabolism occurring in the mitochondria.

The term "operably linked," as used herein, refers to a juxtaposition wherein the components are configured so as to perform their usual function. For example, a mitochondrial targeting agent operably linked to compound will direct the linked compound to be localized to the mitochondria. In some embodiments, the linked compound maintains biological activity in the mitochondria. Alternatively, the compound can be released by cleavage of the linker or functional group that binds the compound to the targeting agent. The functional group or linker can be cleaved by a variety of mechanisms including hydrolysis and enzymatic cleavage.

The term "prodrug," as used herein, refers to a pharmacological substance (drug) which is administered in an inactive (or significantly less active) form. Once administered, the prodrug is metabolized in the body (in vivo) into the active compound.

The term "creatine subunit," as used herein, refers to a portion of a compound having a chemical structure derived from creatine. Creatine subunits typically include a guanidine or modified guanidine moiety, a spacer group, and a functional group. Representative creatine subunits as shown below:

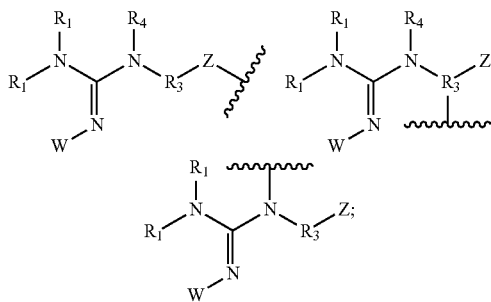

wherein the variables are as defined above.

The term "spacer group," as used herein, refers to a portion of the creatine subunit which connects the guanidine or modified guanidine moiety to the functional group.

The term "linker" or "linking group," as used herein, refer to a group or moiety which is at minimum bivalent, and connects a creatine subunit to an agent. The linker can be composed of any assembly of atoms, including oligomeric and polymeric chains; however, the total number of atoms in the spacer group is particularly between 3 and 200 atoms, more particularly between 3 and 150 atoms, more particularly between 3 and 100 atoms, most particularly between 3 and 50 atoms. In some embodiments, the linker is hydrophilic. In some embodiments, the linker is an alkyl group, an alkylaryl group, an oligo- or polyethylene glycol chain, or an oligo- or poly(amino acid) chain. In some embodiments, the linker may also include one or more cleavable subunits, such as a disulfide group, one or more hydrolysable functional groups, such as an ester or amide, one or more metal complexes, such as a polyhistidine-nickel chelate complex, one or more hydrogen bond donor-acceptor pairs, one or more biomolecule/bioconjugate pairs (such as biotin-avidin or biotin-streptavidin pair), as well as combinations thereof.

The term "therapeutically effective," as used herein, means that the amount of the composition used is of sufficient quantity to ameliorate one or more causes or symptoms of a disease or disorder. Such amelioration only requires a reduction or alteration, not necessarily elimination. As used herein, the terms "therapeutically effective amount" "therapeutic amount" and "pharmaceutically effective amount" are synonymous. One of skill in the art could readily determine the proper therapeutic amount.

The terms "analog" and "derivative" are used herein interchangeably and refer to a compound having a structure similar to that a parent compound, but varying from the parent compound by a difference in one or more certain components. The analog or derivative can differ from the parent compound in one or more atoms, functional groups, or substructures, which are replaced with other atoms, groups, or substructures. An analog or derivative can be imagined to be formed, at least theoretically, from the parent compound via some chemical or physical process.

Generally, a linker (D) connects a single agent (E) to the creatine subunit. In other cases, a creatine subunit is connected to multiple agents. In such compounds, the multiple agents may be the same or different. In some embodiments, multiple agents are connected to a single linker, which is connected to a creatine subunit. In other embodiments, the creatine subunit is substituted at multiple locations with one or more agents, optionally connected via a linker.

In the case of modified creatine compounds, the creatine subunit, linker, and one or more agents can be any of those described below. In some cases, agent is a targeting agent which functions to selectively localize the modified creatine moiety within a cell. In some embodiments, the modified creatine compound contains a creatine subunit operably linked to a mitochondrial targeting agent.

In some embodiments, modified creatine compounds contain a creatine subunit attached to a mitochondrial targeting agent. In some cases, the creatine subunit is directly attached to the mitochondrial targeting agent. In other embodiments, the mitochondrial targeting agent is attached to the creatine subunit through a linker. The linker can be connected to any portion of the creatine subunit, such as to the guanidine moiety, the spacer group, or the functional group.

The modified creatine compounds can be targeted to selectively localize within a cell by linking the creatine compounds to a targeting agent. In one embodiment, the modified creatine compounds contain a creatine subunit linked, attached, conjugated, associated with, or functionalized to one or more mitochondrial targeting agents. In some instances, the creatine moiety retains its biological activity when linked to the targeting agent.

In some embodiments, upon entering the mitochondria, the creatine moiety is cleaved from the targeting agent. The creatine moiety can be released by a variety of mechanisms including simple hydrolysis or enzymatically. In one embodiment, the creatine moiety is bound directly to the targeting agent and the creatine moiety is released hydrolytically and/or enzymatically. In another embodiment, the creatine moiety is bound to the targeting agent via a linker and the linker is cleaved hydrolytically and/or enzymatically.

In some embodiments, the linker is a non-peptide linker which is cleaved within the mitochondria. In other embodiments, the linker is a peptide linker which is cleaved within the mitochondria. In still other embodiments, the creatine moiety is not cleaved from the targeting agent, provided the creatine moiety retains the desired biological activity.

Exemplary modified creatine compounds include, but are not limited to:

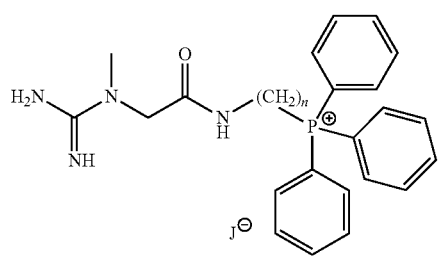

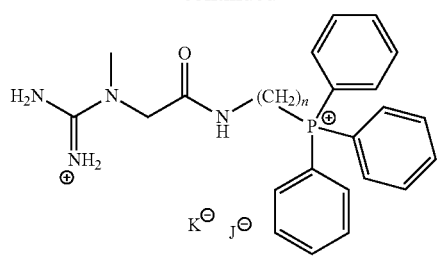
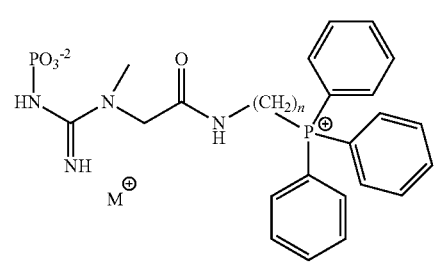
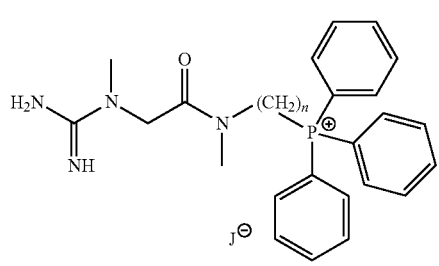
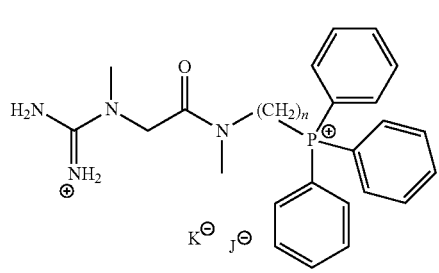
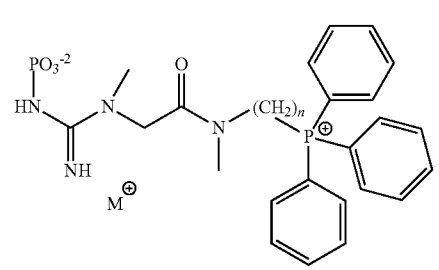
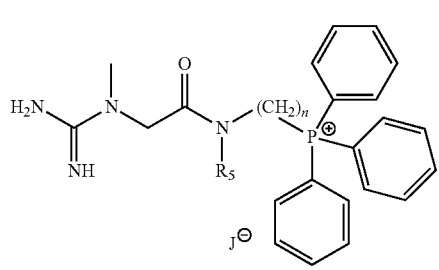
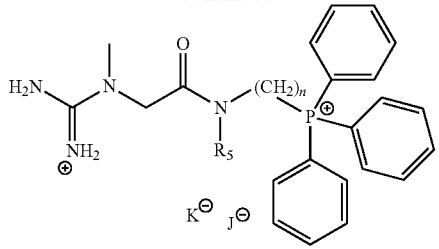
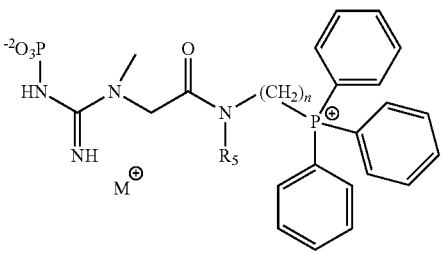
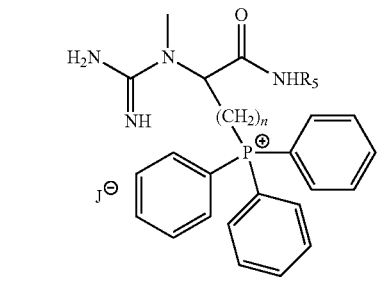
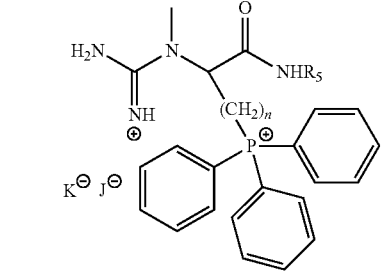
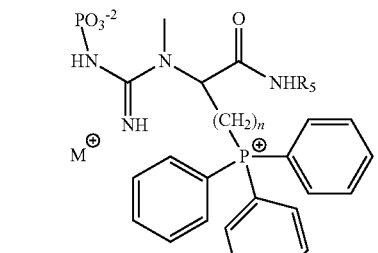
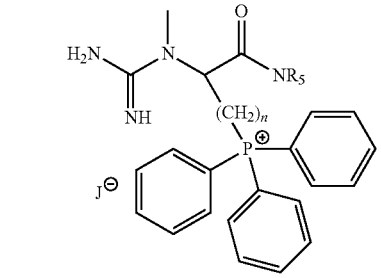

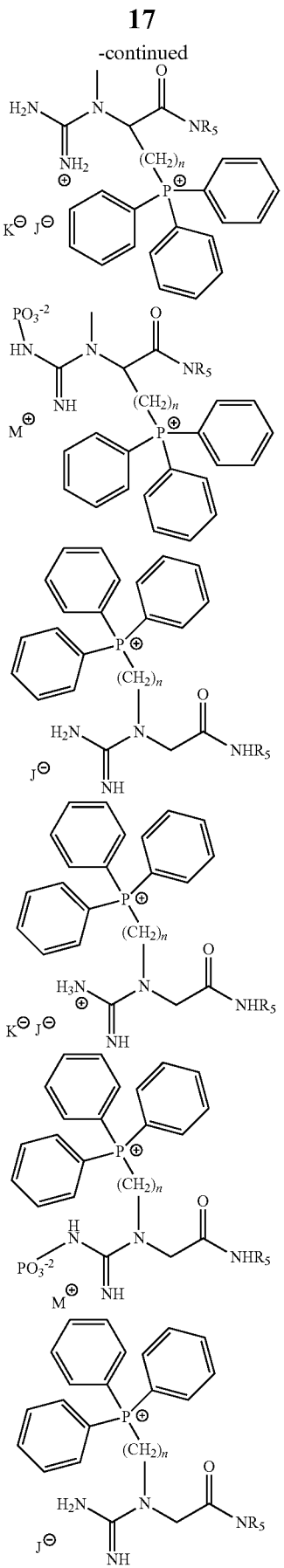
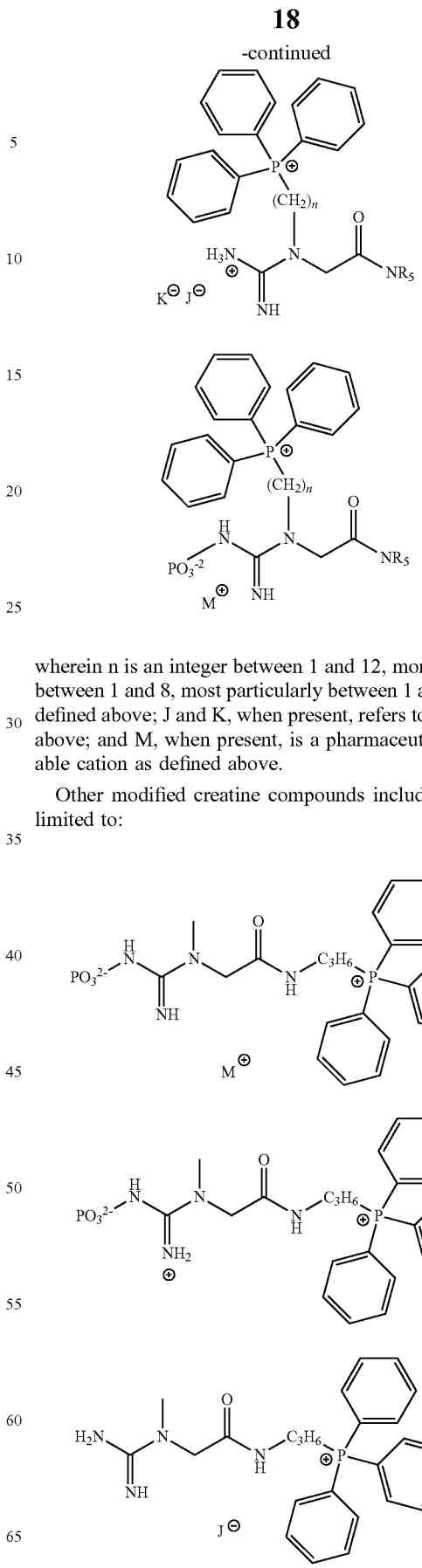
wherein n is an integer between 1 and 12, more particularly between 1 and 8, most particularly between 1 and 6; $R_5$ is as defined above; J and K, when present, refers to X as defined above; and M, when present, is a pharmaceutically acceptable cation as defined above.
Other modified creatine compounds include but are not limited to:
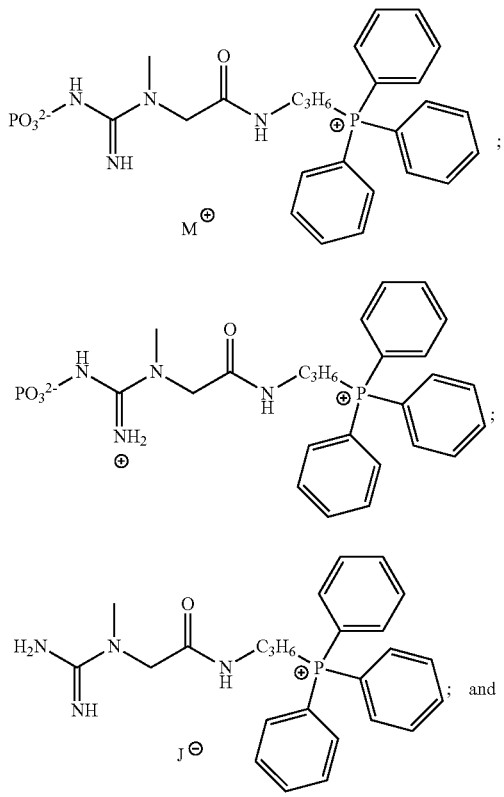

-continued

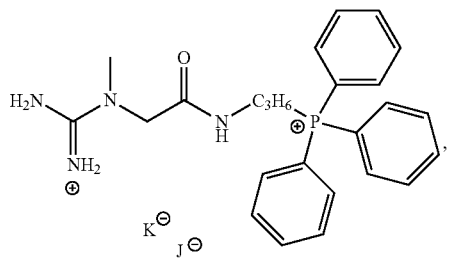

(5)

(10)

wherein M, J and K are as defined above.

In some embodiments, a modified creatine compound of Formula I is found in Table 1.

TABLE 1

| Structure | Name |
|---|---|
| 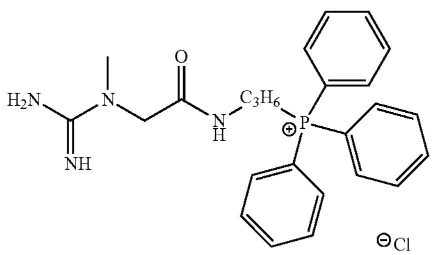 | $N^2$-[amino(imino)methyl]-$N^2$-methyl-N-[3-(triphenylphosphonio)propyl]glycinamide chloride |
| 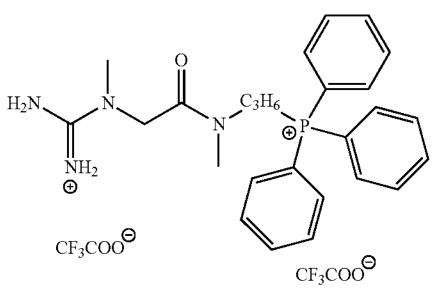 | $N^2$-[ammonio(imino)methyl]-N,$N^2$-dimethyl-N-[3-(triphenylphosphonio)propyl]glycinamide bis(trifluoroacetate) |
| 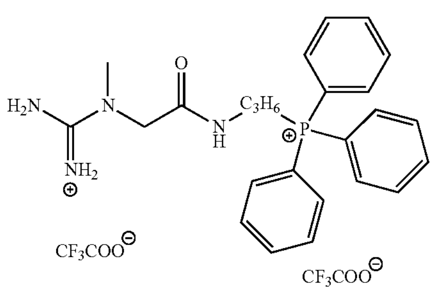 | $N^2$-[ammonio(imino)methyl]-$N^2$-methyl-N-[3-(triphenylphosphonio)propyl]glycinamide bis(trifluoroacetate) |
| 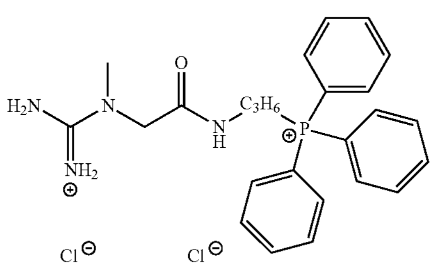 | N2-[ammonio(imino)methyl]-N2-methyl-N-[3-(triphenylphosphonio)propyl]glycinamide dichloride |

TABLE 1-continued

| Structure | Name |
|---|---|
| | N³-[ammonio(imino)methyl]-N³-methyl-N[4-(triphenylphosphonio)butyl]-β-alaninamide bis(trifluoroacetate) |
| 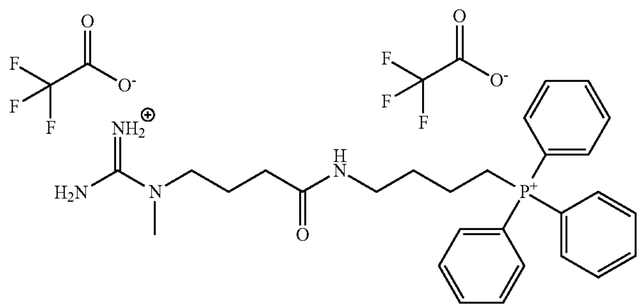 [SMILES: O=C([O-])C(F)(F)F ; CN(CCCC(=O)NCCCC[P+](c1ccccc1)(c1ccccc1)c1ccccc1)C(N)=[NH2+] ; O=C([O-])C(F)(F)F] | {4-[(4-{[ammonio(imino)methyl](methy)amino}butanoyl)amino]butyl}(triphenyl)phosphonium bis(trifluoroacetate) |
| | {4-[(4-{[ammonio(imino)methyl](methyl)amino}-2,2-dimethylbutanoyl)amino]butyl}(triphenyl)phosphonium bis(trifluoroacetate) |
| 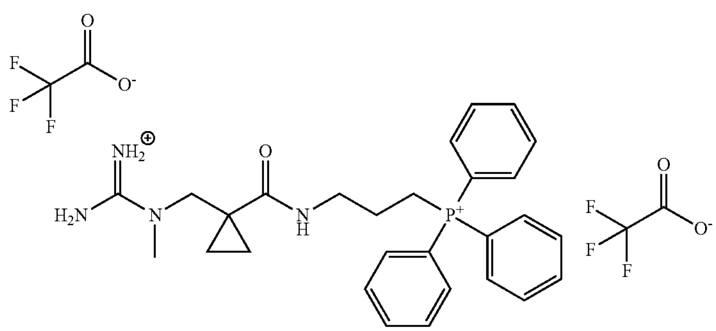 [SMILES: O=C([O-])C(F)(F)F ; CN(CC1(C(=O)NCCC[P+](c2ccccc2)(c2ccccc2)c2ccccc2)CC1)C(N)=[NH2+] ; O=C([O-])C(F)(F)F] | [3-({[1-({[ammonio(imino)methyl](methyl)amino}methyl)cyclopropyl]carbonyl}amino)propyl](triphenyl)phosphonium bis(trifluoroacetate) |
| 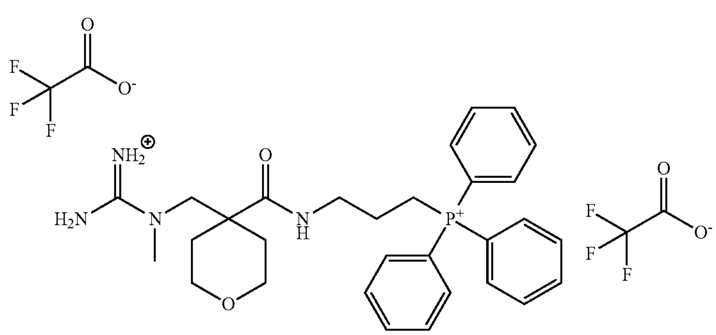 [SMILES: O=C([O-])C(F)(F)F ; CN(CC1(C(=O)NCCC[P+](c2ccccc2)(c2ccccc2)c2ccccc2)CCOCC1)C(N)=[NH2+] ; O=C([O-])C(F)(F)F] | [3-({[4-({[ammonio(imino)methyl](methyl)amino}methyl)tetrahydro-2H-pyran-4-yl]carbonyl}amino)propyl](triphenyl)phosphonium bis(trifluoroacetate) |

In certain embodiments, the modified creatine compounds are therapeutically active in their dosed structural form. In some cases, the dosed structural form serves as a pro-drug, which reacts or is metabolized in vivo to form a compound which is therapeutically active. In such cases it is possible that both the pro-drug and the liberated drug each intrinsically possess activity, although typically at significantly different levels of potency. For example, it is known in the art that ester and amide groups can react in vivo to form carboxylic acids. It is known that guanidine groups (such as the guanidine group of creatine) can undergo phosphorylation in vivo.

The modified creatine compound may be cationic as a consequence of the mitochondrial targeting agent. For example, in some embodiments, the modified creatine compound contains a mitochondrial targeting agent which includes a cationic phosphonium group (e.g., a phosphorous atom substituted by four carbon groups). In cases where a quaternary cationic atom is an intrinsic component of the modified creatine compound, a complementary anionic counter-ion will be present. In some cases, the anionic counter-ion is also an intrinsic component of the modified creatine compound (i.e., the compound is an inner salt). For example, the modified creatine compound can also include a charged carboxylate or phosphate group. In some cases, a distinct ion species will serve as an anionic counter ion. In embodiments where a distinct anionic counter-ion is present, the anionic counter-ion can be a pharmaceutically acceptable anionic counter-ion chosen to confer desirable pharmaceutical properties, such as solubility, upon the modified creatine compound. In certain such embodiments, the anionic counter-ion is a chloride anion.

The modified creatine compounds include a guanidine moiety. The guanidine moiety is basic, and may be protonated by treatment with a pharmaceutically acceptable Bronstead acid.

The modified creatine compounds provided above may have one or more chiral centers and thus exist as one or more stereoisomers. Such stereoisomer-containing compounds can exist as a single enantiomer, a mixture of enantiomers, a mixture of diastereomers, or a racemic mixture.

Modified creatine compounds can be prepared from any suitable creatine subunit. In some embodiments, the creatine subunit is covalently tethered to a mitochondrial targeting agent. Creatine analogs including, but not limited to, the analogs shown in Table 2 below, can serve as a creatine subunit in functionalized creatine compounds. In certain embodiments of Formula I, the mitochondrial targeting agent is covalently coupled to creatine or a creatine analog via a carboxylic acid group. In some embodiments of Formula I, the creatine or creatine analog is covalently coupled to the mitochondrial targeting agent via an ester or amide linkage. In certain embodiments of Formula I, the creatine or creatine analog is covalently coupled to the mitochondrial targeting agent via a secondary or tertiary amide linkage.

TABLE 2

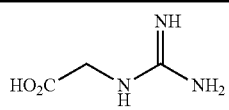

TABLE 2-continued

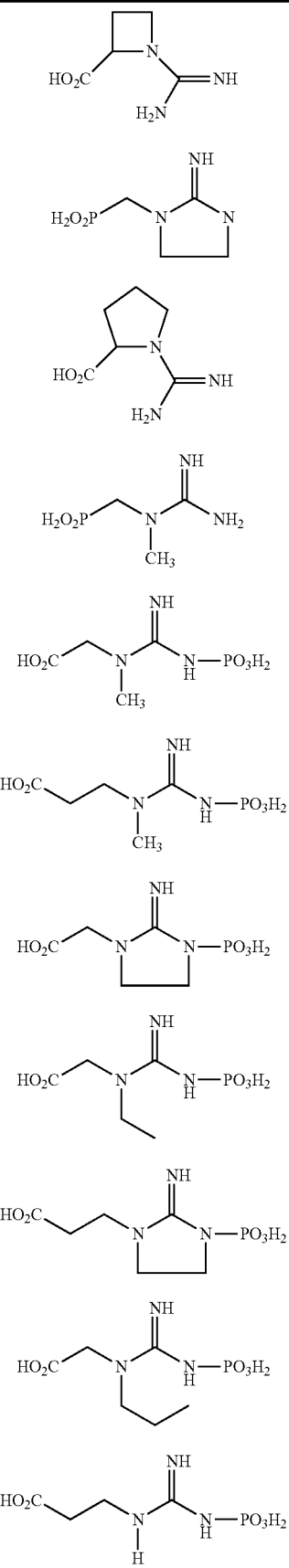

TABLE 2-continued

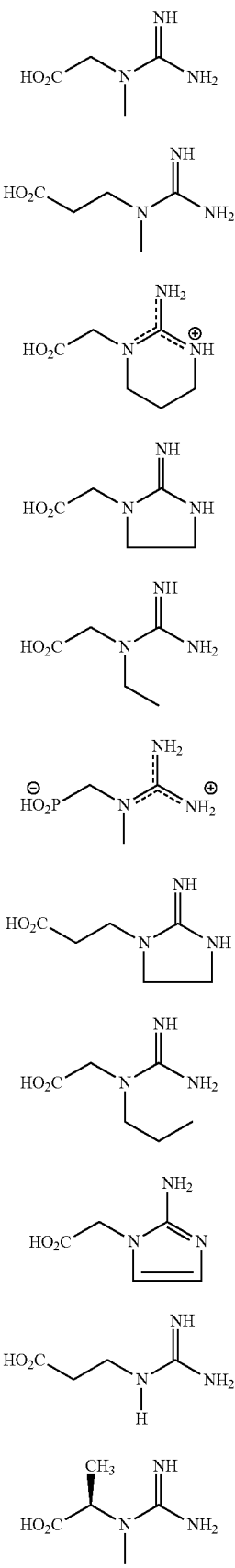

TABLE 2-continued

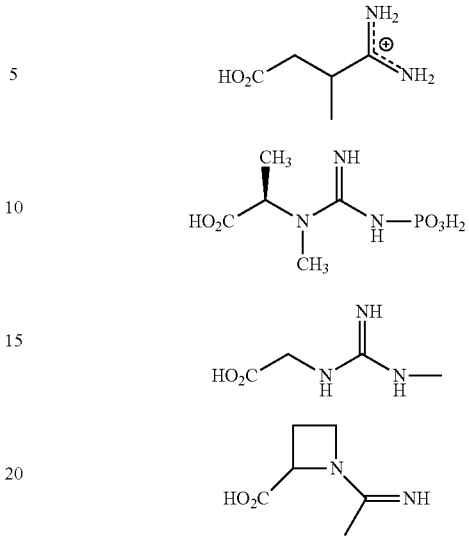

Other exemplary creatine analogs that can be modified to include a mitochondrial targeting agent include, but are not limited to, cyclocreatine (1-carboxymethyl-2-iminoimidazolidine), N-phosphorocreatine (N-phosphoryl creatine), cyclocreatine phosphate (3-phosphoryl-1-carboxymethyl-2-iminoimidazolidine), 1-carboxymethyl-2-aminoimidazole, 1-carboxymethyl-2,2-iminomethylimidazolidine, 1-carboxyethyl-2-iminoimidazolidine, N-ethyl-N-amidinoglycine, and beta-guanidinopropionic acid.

Therapeutic, Diagnostic, Prophylactic, and/or Targeting Agents

Functionalized creatine compounds contain a creatine subunit connected to or associated with one or more agents. Generally, creatine compounds are functionalized with a single agent. Alternatively, creatine compounds can be functionalized with more than one agent. For example, a creatine compound can bound to a linker, optionally containing one or more branch points, to which multiple agents are attached.

In the case of creatine compounds containing a plurality of agents, the agents may be the same or different. In some embodiments, a creatine compound is functionalized with multiple copies of the same agent. In alternative embodiments, a creatine compound is functionalized with a plurality of agents which share the same function (i.e., multiple mitochondrial targeting agents or multiple therapeutic agents). In certain embodiments, a creatine compound is functionalized with a plurality of agents which have at least two different functions (i.e., a plurality of agents which contains one or more targeting agents, for example mitochondrial targeting agents, and one or more therapeutic agents).

The agent may be any substance which is physiologically or pharmacologically active in vivo or in vitro. The agent can be, for example, a substance used for treatment (e.g., therapeutic agent), prevention (e.g., prophylactic agent), diagnosis (e.g., diagnostic agent), cure, or mitigation of disease or illness, a substance which affects the structure or function of the body, a pro-drug which become biologically active or increasingly biologically active after they have been placed in a predetermined physiological environment, or a targeting agent. Examples include, but are not limited to, organic small molecules, peptides, proteins, antibodies, sugars, polysaccharides, and combinations thereof.

In some embodiments, the creatine compounds are functionalized with one or more mitochondrial targeting agents which target the creatine compound to mitochondria. Mitochondrial targeting agents are known in the art, and include lipophilic cations that convey a positive charge to the compound under physiological conditions, such as cationic phosphonium and ammonium groups.

In the case of cationic phosphonium and ammonium groups, the selection of carbon substituents on the cationic atom will affect the target activity, the ability of the therapeutic drug to localize within the mitochondria, and the pharmacokinetic properties (ADME) of the drug. Generally, the substituents on the cation are chosen to distribute the localization of the positive charge and to provide a lipophilic environment in the vicinity of the positive charge to shield the cation from direct interaction with lipophilic biological barriers. Additional pharmacokinetic properties, including oral bioavailability, volume of distribution, and clearance are also dependent on the balance between lipophilic and hydrophilic attributes.

Representative mitochondrial targeting agents can include, but are not limited to, phosphonium groups represented by the general formula —P(R')$_3$$^+$X$^-$, wherein X$^-$ is an anion and R' can be, independently for each occurrence, an alkyl, alkylaryl, alkylcycloalkyl, heterocycloalkyl, alkylheterocycloalkyl, and aryl group, optionally substituted with between one and five substituents selected from alkyl, aldylaryl, cycloalkyl, aryl, hydroxy, alkyl ether, aryl ether, nitrile, fluorine, chlorine, bromine, CF$_3$, thioether, amide, urea, ester, and carbamate. Particularly, between two and three of the R groups are aryl groups. In cases where alkylaryl and/or aryl substituents are attached to the phosphonium ion, the aryl component is particularly a phenyl or a 5-6 membered heteroaryl ring, optionally substituted with between one and two substituents such as halogen, alkyl, alkoxy, CF$_3$, and nitrile. In one embodiment, the mitochondrial targeting agent is an alkyltriphenylphosphonium, tetraphenylphosphonium, or tetraalkylphosphonium group. Suitable alkyltriphenylphosphonium moieties include, but are not limited to, those alkyltriphenylphosphonium moieties containing a C$_1$-C$_6$ straight chain alkylene group having from 1 to 6 carbons, such as a methylene, ethylene, propylene, or butylene group. Suitable tetraalkylphosphonium groups include, but are not limited to those alkyltriphenylphosphonium moieties containing one C$_1$-C$_6$ straight chain alkylene group having from 1 to 6 carbons, such as a methylene, ethylene, propylene, or butylene group, and 3 C$_1$-C$_{18}$ linear, branched, or cyclic alkyl groups.

Other mitochondrial targeting agents include quaternary ammonium groups represented by the general formula —N(R')$_3$$^+$X$^-$, wherein X$^-$ is an anion and R' can be independently for each occurrence, an alkyl, alkylaryl, alkylcycloalkyl, heterocyclo, alkylheterocyclo, and aryl group, optionally substituted with between one and five substituents selected from alkyl, alkylaryl, cycloalkyl, aryl, hydroxy, alkyl ether, aryl ether, nitrile, fluorine, chlorine, bromine, CF$_3$, thioether, amide, urea, ester, and carbamate, including tetraalkylammonium groups, tetraphenylammonium groups, and alkyltriphenylammonium groups. The mitochondrial targeting agent can also be tetraphenylarsonium, Rhodamine G and derivatives thereof, oligo- or polyarginine, oligo- or polylysine, as well as delocalized lipophilic cations containing one to three carbimino, sulfimino, or phosphinimino units as described in Kolomeitsev et al., *Tet. Let.*, Vol. 44, No. 33, 5795-5798 (2003). In some embodiments mitochondrial targeting agents contain a cationic triphenylphosphonium group.

Liphophilic cations are examples of mitochondrial targeting agents because they can pass directly through phospholipid bilayers without requiring a specific uptake mechanism, and they accumulate substantially within mitochondria due to the large membrane potential. The large hydrophobic radius of the triphenylphosphine (TPP) cation enables it to pass easily through the phospholipid bilayer relative to other cations. In one embodiment, the disclosed compounds include TPP derivatives modified to increase hydrophobicity. For example, the hydrophobicity of the targeting agent can be increased by increasing the length of the carbon chain linker, as described in Asin-Cayuela et al., *FEBS Lett.*, 30:571 (1-3), 9-16 (2004). Without wishing to be bound to one theory, it is believed that lipophilic cations are taken up from a positively charged cellular compartment into a negatively charged compartment until a sufficiently large concentration gradient is built up to equalize the electrochemical potential of the molecules in the two compartments. For every 60 mV increase in membrane potential, there will be approximately tenfold accumulation of the lipophilic cation within mitochondria. Because the plasma membrane has a negative 30-60 mV potential on the inside, lipophilic cations will accumulate 5 to 10 fold in the cytosol. Lipophilic cations within the cytosol will accumulate in mitochondria because the mitochondrial membrane potential is typically about 140 to 180 mV.

The mitochondrial targeting agent can also be a polypeptide, such as a positively charged amino acid. Protein transduction domains (PTD), also known as a cell penetrating peptides (CPP), are polypeptides including positively charged amino acids. Therefore, the mitochondrial targeting agent can be a PTD or a CPP. "Protein Transduction Domain" refers to a polypeptide, polynucleotide, carbohydrate, or organic or inorganic compound that facilitates traversing a lipid bilayer, micelle, cell membrane, organelle membrane, or vesicle membrane. A PTD attached to the compounds disclosed herein facilitates the molecule traversing membranes, for example, going from extracellular space to intracellular space, or cytosol to within an organelle such as the mitochondria. PTDs are known in the art, and include, but are not limited to, small regions of proteins that are able to cross a cell membrane in a receptor-independent mechanism (Kabouridis, P., *Trends in Biotechnology* (11):498-503 (2003)). Although several PTDs have been documented, the two most commonly employed PTDs are derived from TAT protein of HIV (Frankel and Pabo, *Cell*, 55(6):1189-93 (1988)) and Antennapedia transcription factor from Drosophila, whose PTD is known as Penetratin (Derossi et al., *J Biol Chem.*, 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ. ID. NO. 1)) of the parent protein that appears to be critical for uptake. Additionally, the basic domain Tat(49-57) or RKKRRQRRR (SEQ. ID NO. 2) has been shown to be a PTD. In the current literature, TAT has been favored for fusion to proteins of interest for cellular import. Several modifications to TAT, including substitutions of Glutatmine to Alanine, i.e., Q→A, have demonstrated an increase in cellular uptake anywhere from 90% (Wender et al., *Proc*

Natl Acad Sci USA., 97(24):13003-8 (2000)) to up to 33 fold in mammalian cells. (Ho et al., Cancer Res., 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include but are not limited to poly-Arg-RRRRRRR (SEQ. ID. NO.: 3); PTD-5-RRQRRTSKLMKR (SEQ. ID. NO.: 4); Transportan GWTLNSAGYLLGKINLKALAALAKKIL (SEQ. ID. NO.: 5); KALA-WEAKLAKALAKALAKHLAKALAKA-LKCEA (SEQ. ID. NO.: 6); and RQIKIWFQNRRMKWKK (SEQ. ID. NO.: 7).

Mitochondrial targeting agents can include short peptide sequences (Yousif, et al., Chembiochem., 10(13):2131 (2009)), for example mitochondrial transporters-synthetic cell-permeable peptides, also known as mitochondria-penetrating peptides (MPPs), that are able to enter mitochondria. MPPs are typically cationic, but also lipophilic; this combination of characteristics facilitates permeation of the hydrophobic mitochondrial membrane. For example, MPPs can include alternating cationic and hydrophobic residues (Horton, et al., Chem Biol., 15(4):375-82 (2008)). Some MPPs include delocalized lipophilic cations (DLCs) in the peptide sequence instead of, or in addition to natural cationic amino acids (Kelley, et al., Pharm. Res., 2011 Aug. 11 [Epub ahead of print]). Other variants can be based on an oligomeric carbohydrate scaffold, for example attaching guanidinium moieties due to their delocalized cationic form (Yousif, et al., Chembiochem., 10(13):2131 (2009).

Mitochondrial targeting agents also include mitochondrial localization signals or mitochondrial targeting signals. Many mitochondrial proteins are synthesized as cytosolic precursor proteins containing a leader sequence, also known as a presequence, or peptide signal sequence. Typically, cytosolic chaperones deliver the precursor protein to mitochondrial receptors and the General Import Pore (GIP) (Receptors and GIP are collectively known as Translocase of Outer Membrane or TOM) at the outer membrane. Typically, the precursor protein is translocated through TOM, and the intermembrane space by small TIMs to the TIM23 or 22 (Translocase of Inner Membrane) at the inner membrane. Within the mitochondrial matrix the targeting sequence is cleaved off by mtHsp70.

Mitochondrial localization/targeting signals generally have of a leader sequence of highly positively charged amino acids. This allows the protein to be targeted to the highly negatively charged mitochondria. Unlike receptor: ligand approaches that rely upon stochastic Brownian motion for the ligand to approach the receptor, the mitochondrial localization signal of some embodiments is drawn to mitochondria because of charge.

As discussed above, in order to enter the mitochondria, a protein generally must interact with the mitochondrial import machinery, consisting of the TIM and TOM complexes (Translocase of the Inner/Outer Mitochondrial Membrane). With regard to the mitochondrial targeting signal, the positive charge draws the linked protein to the complexes and continues to draw the protein into the mitochondria. The Tim and Tom complexes allow the proteins to cross the membranes. Accordingly, one embodiment of the present disclosure delivers compositions of the present disclosure to the inner mitochondrial space utilizing a positively charged targeting signal and the mitochondrial import machinery. In another embodiment, PTD-linked compounds containing a mitochondrial localization signal do not seem to utilize the TOM/TIM complex for entry into the mitochondrial matrix, see Del Gaizo et al. Mol Genet Metab. 80(1-2):170-80 (2003). Mitochondrial localization signals are known in the art, see for example, U.S. Published Application No. 2005/0147993.

Other mitochondrial targeting agents include compounds that are actively transported into the mitochondria, bind to a mitochondria-specific protein, and/or show preferential affinity to a mitochondria-specific lipid such as phospholipid CL. For example, the mitochondrial targeting agent can be a membrane-active cyclopeptide antibiotic, such as gramicidin S, or a segment thereof. Antibiotics of this type have a high affinity for bacterial membranes. Therefore, because of the close relationship between bacteria and mitochondrial membranes, membrane-active cyclopeptide antibiotics, or a segment thereof, also have a high affinity for mitochondrial membrane, and can be used to preferentially target cargo to the mitochondria (Fink, et al., Crit. Care. Med., 35(Suppl): S461-7 (2007).

Other suitable mitochondrial targeting agents are known in the art, see for example, Frantz and Wipf, Environ Mol Mutagen., 51(5): 462-475 (2010), (Yousif, et al., Chembiochem., 10(13):2131 (2009), and Galley, Crit Care, 14(4):230 (pages 1-9) (2010). Particularly, the mitochondrial targeting agent does not permanently damage the mitochondrion, for example the mitochondrial membrane, or otherwise impair mitochondrial function.

Modified creatine compounds disclosed can optionally contain a linker which connects the creatine subunit to the agent. The linker can be inert, or the linker can have biological activity. The linker must be at minimum bivalent; however, in some embodiments, the linker can be bound to more than one active agent, in which case, the linker is polyvalent.

The linker can be composed of any assembly of atoms, including oligomeric and polymeric chains which functions to connect the agent to the creatine subunit. In some cases, the linker is an oligomeric and polymeric chain, such as an oligo- or polyethylene glycol chain, or an oligo- or poly (amino acid) chain. Peptide linkers include peptides that can be cleaved once the compound enters the mitochondria. For example, in some cases, the peptide linker is a mitochondrial localization signal, as discussed in detail above. In other cases, the linker is a non-polymeric organic functional group, such as an alkyl group or an alkylaryl group. In these embodiments, the total number of atoms in the linker is less than 250 atoms, between 3 and 200 atoms, or between 3 and 150 atoms, or between 3 and 100 atoms, or between 3 and 50 atoms, or between 3-12 atoms. In some embodiments, the linker is hydrophilic to facilitate passage of the creatine compound across biological membranes.

In many cases, the linker is a linear chain. In some embodiments, however, the linker contains one or more branch points. In the case of branched linker, the terminus of each branch point can be functionalized with an agent. In one such embodiment, a dendritic linker is used, with the creatine subunit being bound to the focal point of the dendrimer, and multiple agents are bound to the ends of the dendritic branches.

In some embodiments, the linker includes one or more cleavable subunits, such as a disulfide group, a hydrazone group, or a peptide group, which can be cleaved by proteolytic enzymes within a cell. In alternative embodiments, the linker contains one or more hydrolysable subunits, such as an ester group. The linker can also contain one or more covalent or non-covalent functional groups to facilitate the assembly and/or separation of the creatine subunit from the attached agent, including, but not limited to, one or more metal complexes, such as polyhistidine-nickel chelate complexes, one or more heteroaromatic rings (such as triazole rings formed by the cycloaddition of an alkyne and an azide), one or more hydrogen bond donor-acceptor pairs, and one or more biomolecule/bioconjugate pairs (such as biotin-avidin or biotin-streptavidin pair), as well as combinations thereof.

Modified creatine compounds contain a functional group which serves to confer creatine-like activity and/or to serve as an attachment point for the linker group. In cases where this serves as an attachment point for the linker group, it is minimum bivalent, and may result in an intrinsically active compound or may serve as a pro-drug.

In some embodiments, the functional group contains one or more heteroatoms selected from the group consisting of oxygen, nitrogen, sulfur, phosphorous, and combinations thereof. Representative functional groups include esters, ethers, ketones, amides, ureas, carbamates, thioesters, thioethers, disulfide bonds, thioamides, thiones, thionoesters, triazole rings, and dithioesters. In some embodiments, the functional group is a secondary amide, tertiary amide, or ester.

In Vitro Assays of Compound Activity

A variety of in vitro assays can be used to determine the ability of the modified creatine compounds to modulate mitochondrial function.

Disclosed herein is an in vitro assay for determining the activity of recombinant CPK on the modified creatine compounds. Recombinant CPK is mixed with ATP and a modified creatine compound of interest. ATP hydrolysis, a measure of the rate of transfer of the gamma phosphate from ATP to the guanidinium groups of the creatine subunit, was measured using luciferase. The rate of ATP hydrolysis/consumption for the modified creatine compound is then compared to the rate of ATP hydrolysis/consumption for creatine.

In some embodiments, the modified creatine compounds induce a higher rate of ATP hydrolysis/consumption than an equimolar concentration of creatine. More particularly, the modified creatine compounds induce a rate of ATP hydrolysis/consumption that is at least 25%, 50%, 75%, 100%, 125%, 150%, 175%, 200%, 225%, 250%, 275%, or 300% greater than the rate of ATP hydrolysis/consumption measured for an equimolar concentration of creatine.

Also described are assays for measuring the ability of a modified creatine compound to alter mitochondrial activity and function. In one assay, the ability of a modified creatine compound to increase the oxygen consumption rate (OCR) of cells is determined. In some embodiments, the modified creatine compound induces a larger increase in the oxygen consumption rate of cells than an equimolar concentration of unmodified creatine. In some embodiments, the modified creatine compound at a 5 nM concentration induces an increase in the oxygen consumption rate of cells that is at least 25%, 50%, 75%, 100%, 125%, 150%, 175%, or 200% greater than the increase in OCR measured for a 10 µM concentration of creatine.

Further described is an assay for measuring the ability of a modified creatine compound to increase Complex I (CI) activity in cells. In some embodiments, the modified creatine compound increases Complex I activity in cells to a greater degree than an equimolar concentration of creatine. In some embodiments, the modified creatine compound at a 25 nM concentration induces at least a 25%, 50%, 75%, 100%, 125%, 150%, 175%, or 200% greater increase in Complex I activity than that induced by a 10 µM concentration of creatine.

Formulations and Dosages

Formulations containing one or more of the compounds described herein or a prodrug thereof may be prepared using a pharmaceutically acceptable carrier composed of materials that are considered safe and effective and may be administered to an individual without causing undesirable biological side effects or unwanted interactions. The carrier comprises all components present in the pharmaceutical formulation other than the active ingredient or ingredients. As generally used herein, "carrier" includes, but is not limited to, diluents, binders, lubricants, disintegrators, fillers, pH modifying agents, preservatives, antioxidants, solubility enhancers, and coating compositions.

Carrier also includes all components of the coating composition, which may include plasticizers, pigments, colorants, stabilizing agents, and glidants. Delayed release, extended release, and/or pulsatile release dosage formulations may be prepared as described in standard references, such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers, such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers, such as plasticizers, pigments, colorants, glidants, stabilization agents, pore formers, and surfactants.

Optional pharmaceutically acceptable excipients present in the drug-containing tablets, beads, granules, or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate, and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration and generally include, but are not limited to, starch, sodium starch glycolate, sodium carboxymethyl starch, sodium carboxymethylcellulose, hydroxypropyl cellulose, pregelatinized starch, clays, cellulose, alginine, gums, and cross linked polymers, such as cross-linked PVP (Polyplasdone XL from GAF Chemical Corp).

Stabilizers are used to inhibit or retard drug decomposition reactions, which include, by way of example, oxidative reactions.

Surfactants may be anionic, cationic, amphoteric or non-ionic surface active agents. Suitable anionic surfactants include, but are not limited to, those containing carboxylate, sulfonate, and sulfate ions. Examples of anionic surfactants include sodium, potassium, ammonium of long chain alkyl sulfonates, and alkyl aryl sulfonates, such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds, such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine, and lauryl sulfobetaine.

If desired, the tablets, beads, granules, or particles may also contain minor amount of nontoxic auxiliary substances, such as wetting or emulsifying agents, dyes, pH buffering agents, or preservatives.

The compositions optionally contain one or more additional active agents. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

Representative antibiotics include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin.

In one embodiment, the concentration of the antibiotic is from about 0.01% to about 20%, particularly from about 1% to about 15%, more particularly from about 6% to about 12%, by weight of the final composition.

Representative examples of non-steroidal anti-inflammatory agents include, without limitation, oxicams, such as piroxicam, isoxicam, tenoxicam, and sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

In one embodiment, the concentration of the non-steroidal anti-inflammatory agent is from about 0.01% to about 20%, particularly from about 1% to about 15%, more particularly from about 6% to about 12% by weight of the final composition.

Representative examples of steroidal anti-inflammatory drugs include, without limitation, corticosteroids, such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

In one embodiment, the concentration of the steroidal anti-inflammatory agent is from about 0.01% to about 20%, particularly from about 1% to about 15%, more particularly from about 6% to about 12%, by weight of the final composition.

Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, framesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

In one embodiment, the concentration of the anti-microbial agent is from about 0.01% to about 20%, particularly from about 1% to about 15%, more particularly from about 6% to about 12%, by weight of the final composition.

For all of the creatine compounds disclosed, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage levels may be lower.

Methods of Treatment

Embodiments of the present disclosure provide compositions and methods for targeted delivery of compounds to mitochondria to modulate mitochondrial function or treat one or more symptoms of a mitochondrial disorder. Suitable mitochondrial disorders that can be treated with the compositions disclosed herein include, but are not limited to, mitochondrial myopathies. Mitochondrial myopathies include Kearns-Sayre syndrome, Leigh's syndrome, mitochondrial DNA depletion syndrome (MDS), mitochondrial encephalomyopathy, lactic acidosis and strokelike episodes (MELAS), myoclonus epilepsy with ragged red fibers (MERRF), mitochondrial neurogastrointestinal encephalomyopathy (MNGIE), neuropathy, ataxia and retinitis pigmentosa (NARP), and progressive external ophthalmoplegia (PEO).

The disclosed compositions can be used to treat one or more symptoms of Cerebral Creatine Deficiency Syndromes, including Guanidinoacetate Methyltransferase Deficiency (GAMT Deficiency), L-Arginine:Glycine Amidinotransferase Deficiency (AGAT Deficiency), and SLC6A8-Related Creatine Transporter Deficiency (SLC6A8 Deficiency).

The disclosed compositions can be used to modulate ATP production in mitochondria by altering the ratio of phosphocreatine/creatine. The ratio of phosphocreatine/creatine can be increased relative to a control by administering the one or more of the disclosed compounds. Increasing the amount of phosphocreatine in the mitochondria increases the ability of the mitochondria to produce ATP. Thus, another embodiment provides a method for increasing mitochondrial production of ATP in a host by administering to the host an effective amount of the disclosed compositions. Increasing the ATP-generating capacity allows a cell to better handle energetic challenges, thus preventing cell damage or death, improving cellular function, increasing cellular healing and replacement, and preventing tumorigenesis.

The disclosed composition can also be used to treat one or more symptoms associated with arthritis, congestive heart failure, disuse atrophy, gyrate atrophy, Huntington's disease, McArdles disease, Alexander disease, Alzheimer's, Parkinson's disease, Amyotrophic lateral sclerosis (ALS), Amino Acid disorders, Ataxias, Barth, Tafazzins, Cardiomyopathy, Carnitine disorders, Cartilage-Hair hypoplasia, Congenital muscular dystrophy, cramps, HAM, Non-syndromic and amino-glycoside induced deafness, DIDMOAD, Deafness-Dystonia, Diabetes, Dystonia, Encephalopathies, Blindness, macular degeneration, Optic atrophy, Wolfram, External Ophthalmoplegia, HyperThyroid, Fatigue, Exercise intolerance, Friedreich ataxia, Hypoglycemia, Leukodystrophy, Maple syrup urine disease, Menkes, Multiple symmetric lipomatosis, Myalgias, Myoglobinuria, Inclusion body myositis, Sensory neuropathy, Occipital horn syndrome, Paraganglioma, Pearson's, Rhabdomyolysis, Spastic paraparesis, Spinal muscular atrophy, Stuve-Wiedemann syndrome, Sudden infant death (SIDS), Wilson's disease, COPD, stroke, cardiac infarction, ischemia, diabetes, and inflammation.

The disclosed compositions can also be used for iatrogenic indications—HAART therapies, amino-glycoside antibiotics, COX-2 inhibitor related cardiac disease, statin myopathy, and cancer cachexia.

One embodiment provides a nutraceutical, including one or more of the disclosed mitochondria-targeted compounds. The nutraceucitcal can be used, for example by performance athletes, for endurance training, muscle/strength building, bone density increase, cognitive function, wound healing, anti-aging, anti-obesity/weight loss, and anti-ROS. The nutraceutical can be administered to healthy or diseased individuals.

Increasing mitochondrial production of ATP can be useful for improving exercises tolerance or stamina and/or muscle strength or stamina. For example, the compositions disclosed herein can be administered to a subject to enhance the ability to sustain high ATP turnover rates during strenuous exercise resulting in delayed neuromuscular fatigue, improved muscle strength, improved muscle power output, improved recovery from exercise, increased body mass, and increased muscle mass, or combinations thereof, compared to a control. In some embodiments, the compositions are administered to inhibit or reduce the effects of sarcopenia, the typical loss of muscle mass that is characteristic of advanced age. For example, the compositions may attenuate age-related muscle atrophy and/or strength loss in a subject compared to a control.

The compositions disclosed herein can also be administered to a subject to improve or increase brain or cognitive performance. Brain/cognitive performance includes, but is not limited to, beneficial effects on mental functions, such as an increase in response to mental training or challenge, reduced mental fatigue, improved task-evoked increase in oxygen utilization, improved recognition memory, increased speed of computation, increased power of computational, and improved general ability (Rae, et al., *Proc. R. Soc. Lond.* 270:2147-2150 (2007)). Increases extracellular ATP may also enhance cerebral blood flow and metabolism, increase mental sharpness, and potentially lessen the perception of fatigue and/or exercise-associated pain in the subject.

Pharmaceutical compositions including the disclosed compounds are provided. The pharmaceutical compositions may be for administration by oral, parenteral (intramuscular, intraperitoneal, intravenous (IV), or subcutaneous injection), transdermal (either passively or using iontophoresis or electroporation), or transmucosal (nasal, vaginal, rectal, or sublingual) routes of administration or by using bioerodible inserts, and can be formulated in dosage forms appropriate for each route of administration. In one embodiment, the compounds are administered orally. In another embodiment, the compounds are administered parenterally in an aqueous solution. In general, pharmaceutical compositions are provided including effective amounts of a creatine compounds or analogs.

The compositions can be formulated for oral delivery. Oral solid dosage forms are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the ABC transporter ligands (or chemically modified forms thereof) and inert ingredients which allow for protection against the stomach environment and release of the biologically active material in the intestine.

Another embodiment provides liquid dosage forms for oral administration, including pharmaceutically acceptable emulsions, solutions, suspensions, and syrups, which may contain other components, including inert diluents; adjuvants such as wetting, emulsifying, and suspending agents; and sweetening, flavoring, and perfuming agents.

The compositions may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. PEGylation is an example of chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane, and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Particularly, the release will avoid the deleterious effects of the stomach environment, either by protection of the peptide (or derivative) or by release of the peptide (or derivative) beyond the stomach environment, such as in the intestine.

To ensure full gastric resistance, a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings or coatings which make the tablet easier to swallow. Capsules may consist of a hard shell (such as gelatin) for delivery of dry therapeutic (i.e. powder). For liquid forms, a soft gelatin shell may be used. The shell material of cachets could be thick starch or other edible paper. For pills, lozenges, molded tablets or tablet triturates, moist massing techniques can be used.

The active ingredient (or derivative) can be included in the formulation as fine multiparticulates in the form of granules or pellets of particle size about 1 mm. The formulation of the material for capsule administration could also be as a powder, lightly compressed plugs, or as tablets. These therapeutics could be prepared by compression.

Colorants and/or flavoring agents may also be included. For example, the composition may be formulated, such as by liposome or microsphere encapsulation, and then further contained within an edible product, such as a refrigerated beverage containing colorants and flavoring agents.

Preparations disclosed here for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are particularly suppositories which may contain, in addition to the active substance, excipients such as cocoa butter or a suppository wax. Compositions for nasal or sublingual administration are also prepared with standard excipients well known in the art.

Preparation of Compounds

Synthesis of alkyltriphenylphosphonium cations are known in the art. See, for example, MP Murphy and RA Smith. *Annu Rev Pharmacol Toxicol.* 2007; 47:629-56 (2007). Creatine analogs are also known in the art. See, for example, United States Patent Application Publication No. US 2006/0128671 to Kaddurah-Daouk, et al.

Creatine compounds functionalized with one or more mitochondrial targeting agents can be synthesized by reacting creatine or a creatine analog with a lipophilic cation. In some embodiments, the creatine subunit and the mitochondrial targeting agent are covalently connected by a linker.

A number of synthetic methods are useful for the preparation of the compounds disclosed herein. Representative methodologies for the preparation of creatine compounds are discussed below. The appropriate route for synthesis of a given creatine compound can be selected in view of the linking group desired, spacer group desired, and the structure of the compound as a whole as it relates to compatibility of functional groups, protecting group strategies, and the presence of labile bonds.

In addition to the synthetic methodologies discussed below, alternative reactions and strategies useful for the preparation of the creatine compounds disclosed herein are known in the art. See, for example, March, "Advanced Organic Chemistry," 5th Edition, 2001, Wiley-Interscience Publication, New York.

The following reaction schemes illustrate the general synthetic procedures of the compounds of the present invention. All starting materials are prepared by procedures described in these schemes or by procedures known to one of ordinary skill in the art.

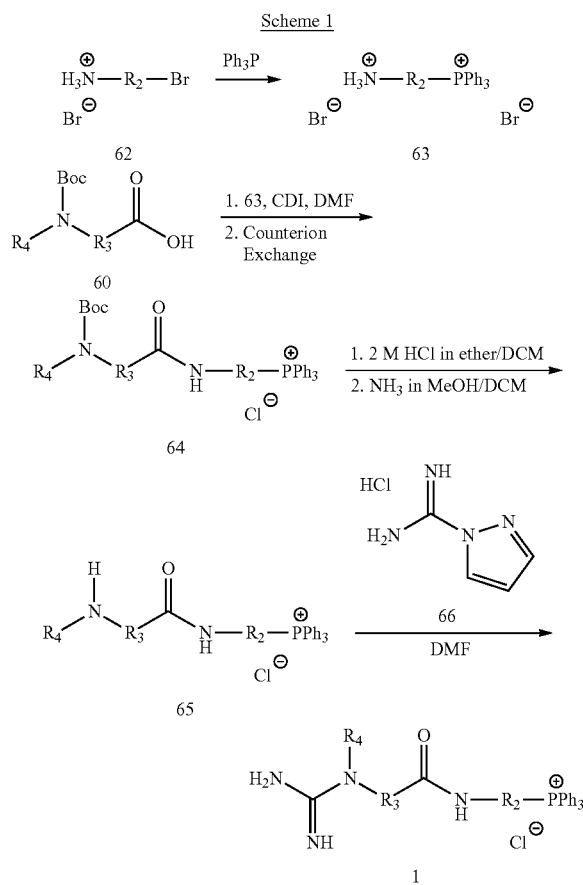

In Scheme 1, $R_2$, $R_3$, and $R_4$ are the same as defined previously. Phosphonium salt 63 can be prepared from commercially available 62 using procedures well known in the art. The structure 63 can then be coupled with Boc-sarcosine 60 in the presence of one of the several commonly used coupling reagents used to synthesize amides, including carbonyldiimidazole (CDI), a carbodimide reagent (e.g. EDC), and PyBOP, in dimethylformamide (DMF) or THF. A workup with an aqueous solution of LiCl and tetrabutylammonium chloride can be used to isolate Boc-protected 64 as the chloride salt. Treatment of 64 with acid such as HCl in ether followed by neutralization with methanolic ammonia deprotects the Boc-protected amine, affording 65. Reaction of 65 with 1H-pyrazole-1-carboximidamide hydrochloride 66 in DMF provides the compound of structure 1 (Castillo-Meléndez et al. Synthesis, 10, 1655 (2004)).

The synthetic methodology described in Scheme 1 can be modified to prepare tertiary amines, such as a compound of structure 2, as shown in Scheme 2.

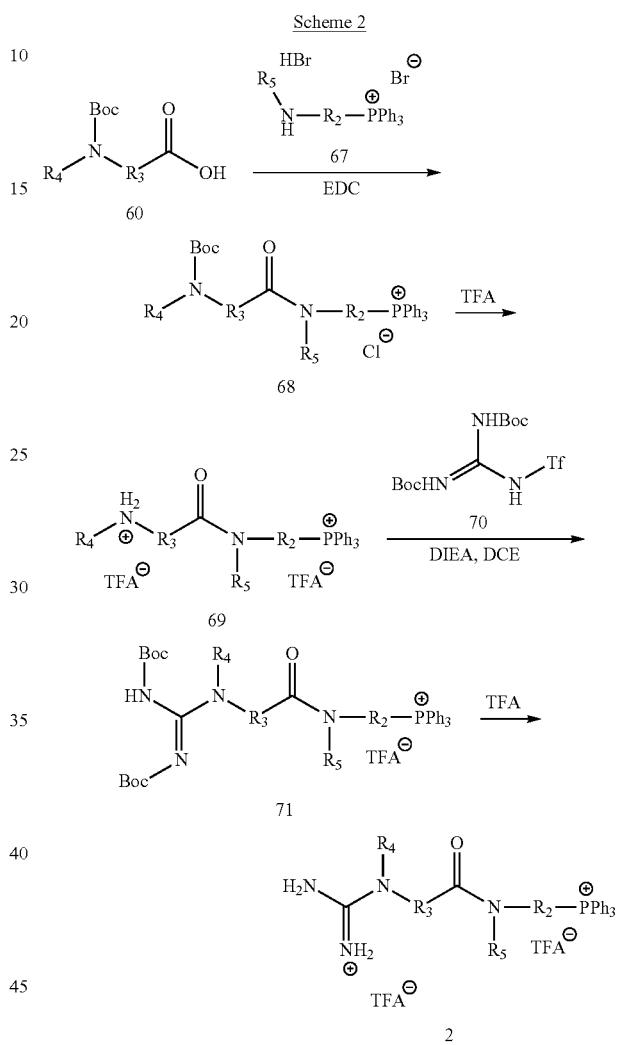

In Scheme 2, $R_2$, $R_3$, $R_4$ and $R_5$ are the same as defined previously. Phosphonium salt 67 can be coupled with Boc-sarcosine 60 in the presence of one of the several commonly used coupling reagents used to synthesize amides, including carbonyldiimidazole (CDI), a carbodimide reagent (e.g. EDC), and PyBOP, in a solvent such as DMF, forming 68. Treatment of 68 with trifluoroacetic acid (TFA) removes the BOC-group affording amine 69. Reaction of 69 with 70 in the presence of N,N-diisopropylethylamine affords compound 71, which can be subsequently deprotected using TFA to provide a compound of structure 2.

Creatine compounds within the scope of Formula II can be prepared by various methodologies. For example, a compound of structure 5, containing an ester functional group, can be prepared using the synthetic strategy described in Scheme 3.

Scheme 3

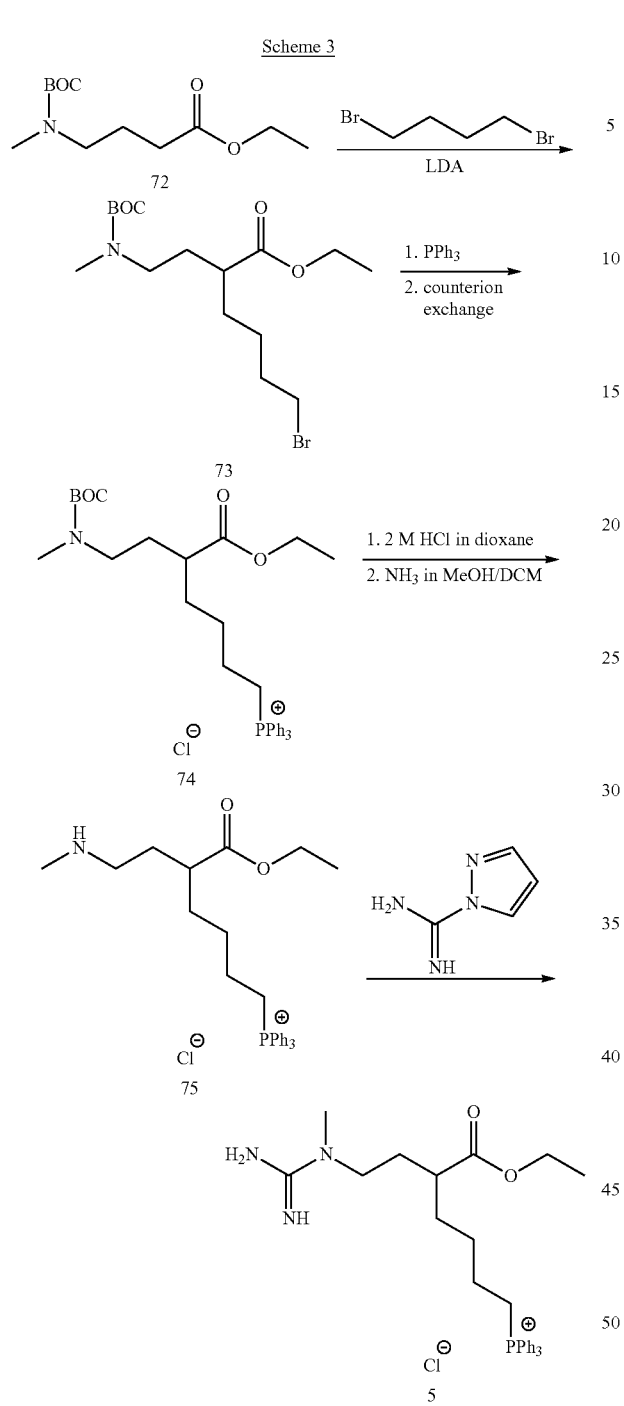

Scheme 4

Using a similar strategy, compound 6, containing a tertiary amide functional group, can be prepared using the synthetic strategy described in Scheme 4.

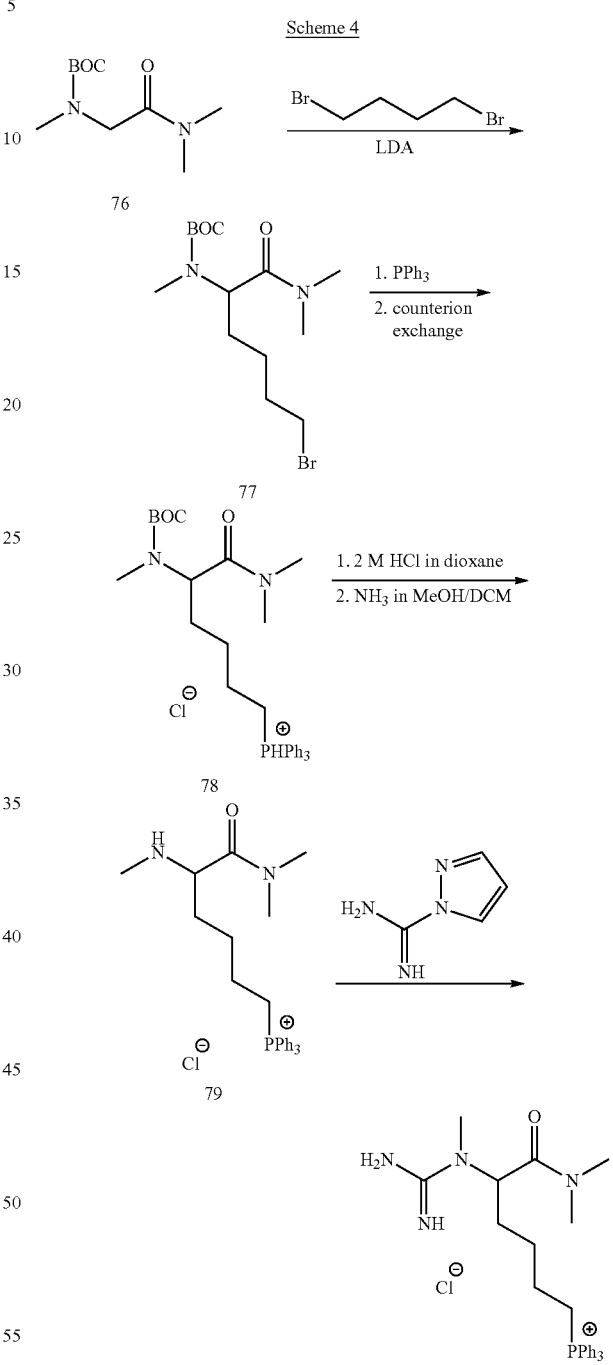

The synthesis of a compound of structure 5 begins with the preparation of 73 by LDA-induced alkylation of 72 with dibromobutane. Following this, 73 can be heated with triphenylphosphine in xylene or dimethoxyethane (DME) using microwave irradiation to form the phosphonium salt. The bromide counterion can then be exchanged for chloride by washing with an aqueous LiCl solution containing tetraammonium chloride, affording 74. Treatment of 74 with 2.0 M HCl in dioxane followed by neutralization with methanolic ammonia provides the deprotected amine 75. Reaction of 75 with 1H-pyrazole-1-carboximidamide hydrochloride in DMF provides modified creatine 5.

The synthesis of a compound of structure 6 begins with preparation of 77 by LDA-induced alkylation of BOC-sarconsine dimethyl amide 76 with dibromobutane. Following this, intermediate 77 can be heated with triphenylphosphine in xylene or dimethoxyethane (DME) using microwave irradiation to generate the phosphonium salt. The bromide counterion can be exchanged for chloride counterion by washing with an aqueous LiCl solution containing tetraammonium chloride, affording 78. Treatment of 78 with 2.0 M HCl in dioxane followed by neutralization with methanolic ammonia will provide the deprotected amine 79. Reaction of 79 with 1H-pyrazole-1-carboximidamide hydrochloride in DMF will form modified creatine 6.

Modified creatine compounds within the scope of Formula III can be prepared by various methodologies known in the art. For example, modified creatine a compound or structure 7 can be prepared as described in Scheme 5.

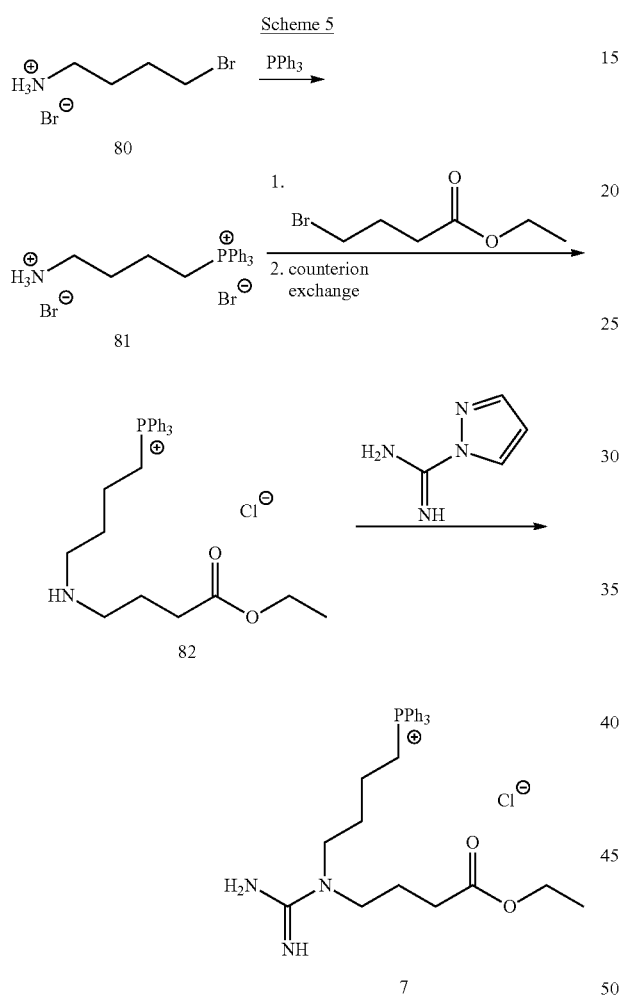

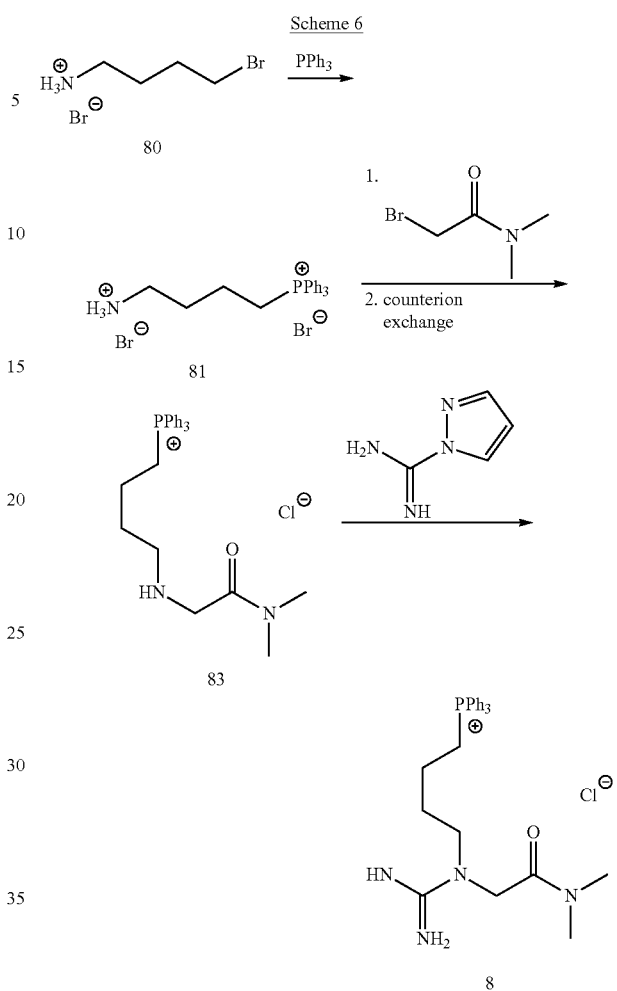

The synthesis of a compound of structure 7 can begin with preparation of amine 81 by reaction of 80 with triphenylphosphine in n-butanol at 120° C. Following purification, 81 can be treated with ethyl bromoacetate in the presence of diisopropylethylamine using acetonitrile as solvent. Following workup, the counterion can be exchanged using an aqueous LiCl solution containing tetrabutylammonium chloride. This affords compound 82. Reaction of 82 with 1H-pyrazole-1-carboximidamide hydrochloride in DMF will provide modified creatine compound 7.

Using a similar strategy, compound 8, containing a tertiary amide functional group, can be prepared using the synthetic strategy described in Scheme 6.

The synthesis of 8 can begin with preparation of amine 81 by reaction of 80 with triphenylphosphine in n-butanol at 120° C. Following purification, 81, can be treated with 2-bromo-N,N-dimethylacetamide in the presence of diisopropylethylamine. Following workup, the counterion can be exchanged using an aqueous LiCl solution containing tetrabutylammonium chloride. This will afford compound 83. Reaction of 83 with 1H-pyrazole-1-carboximidamide hydrochloride in DMF will provide modified creatine compound 8.

EXAMPLES

Example 1

Preparation of $N^2$-[ammonio(imino)methyl]-$N^2$-methyl-N-[3-(triphenylphosphonio)propyl]glycinamide bis(trifluoroacetate)

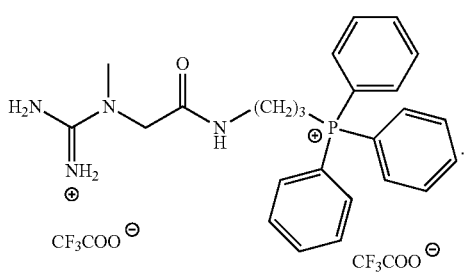

Step 1. Preparation of (3-aminopropyl)(triphenyl)phosphonium bromide hydrobromide (3-bromopropyl)(triphenyl)phosphonium bromide (4.9 g, 10.0 mmol) was treated with 7 M ammonia in methanol (97 mL, 680 mmol) in a sealed tube. The mixture was heated at 85° C. for 4 hours and cooled to room temperature. The volatiles were removed, and the resultant semi-solid was purified on a silica gel column eluting with first with 20% methanol in methylene chloride followed by 25% 1 M ammonia in methanol and methylene chloride to give the title compound (2.07 g) in a 41% yield.

Step 2. Preparation of ethyl N—{(E)-[(tert-butoxycarbonyl)amino][(tert-butoxycarbonyl)imino]methyl}-N-methylglycinate Di-tert-butyl {[(trifluoromethyl)sulfonyl]carbonimidoyl} biscarbamate (di-Boc-triflylguanidine) (738 mg, 1.88 mmol) was charged to a flame dried flask and taken up in anhydrous 1,2-dichloroethane (7.4 mL). Then triethylamine (579 µL, 4.15 mmol) and ethyl N-methylglycinate hydrochloride (312 mg, 2.03 mmol) were added. The mixture was stirred at 50° C. for 5 hours and cooled to room temperature. The reaction was diluted with methylene chloride and washed with 2 M aqueous sodium bisulfate, aqueous sodium bicarbonate, and dried over anhydrous sodium sulfate. The organic was concentrated, and the crude product was purified on a silica gel column eluting with 50% ethyl acetate in hexanes to give the title compound in a 71% yield.

Step 3. Preparation of N—{(E)-[(tert-butoxycarbonyl)amino][(tert-butoxycarbonyl)imino]methyl}-N-methylglycine Ethyl N—{(E)-[(tert-butoxycarbonyl)amino][(tert-butoxycarbonyl)imino]methyl}-N-methylglycinate (630 mg, 1.75 mmol) was dissolved in tetrahydrofuran (6.3 mL) at room temperature. To this was added 1.0 M aqueous sodium hydroxide (0.75 mL, 1.75 mmol). The mixture was stirred at room temperature for 1 hour and then concentrated under vacuum to remove the tetrahydrofuran. The mixture was cooled in an ice bath and acidified with 1 M aqueous sulfuric acid (1.72 mL, 1.75 mmol). The mixture was diluted with methylene chloride, and then the water was removed using anhydrous magnesium sulfate. After filtering, the methylene chloride was removed under vacuum to give the title compound in a quantitative yield.

Step 4. Preparation of $N^2$—{(E)-[(tert-butoxycarbonyl)amino][(tert-butoxycarbonyl)imino]methyl}-$N^2$-methyl-N-[3-(triphenylphosphonio)propyl]glycinamide bromide N—{(E)-[(tert-butoxycarbonyl)amino][(tert-butoxycarbonyl)imino]methyl}-N-methylglycine (304 mg, 0.63 mmol) and (3-aminopropyl)(triphenyl)phosphonium bromide hydrobromide (209 mg, 0.63 mmol) were taken up in methylene chloride (3.0 mL) and treated with N,N-diisopropylethylamine (340 µL, 1.96 mmol) and 1-hydroxybenzotriazole hydrate (101 mg, 0.66 mmol). After all the solids dissolved, the reaction as treated with N-(3-dimethylaminopropyl)-N'-ethylcarbodiimide hydrochloride (375 mg, 1.96 mmol) and stirred at room temperature overnight. The reaction was diluted with methylene chloride, and the organic layer was washed with aqueous sodium bicarbonate and water and then dried over anhydrous sodium sulfate. After filtration, concentration of the organic gave crude $N^2$—{(E)-[(tert-butoxycarbonyl)amino][(tert-butoxycarbonyl)imino]methyl}-$N^2$-methyl-N-[3-(triphenylphosphonio)propyl]glycinamide bromide (390 mg) in a 68% yield, which was used crude in the subsequent step.

Step 5. Preparation of $N^2$-[ammonio(imino)methyl]-$N^2$-methyl-N-[3-(triphenylphosphonio)propyl]glycinamide bis(trifluoroacetate)

$N^2$—{(E)-[(tert-butoxycarbonyl)amino][(tert-butoxycarbonyl)imino]methyl}-$N^2$-methyl-N-[3-(triphenylphosphonio)propyl]glycinamide bromide (290 mg, 0.41 mmol) was dissolved in trifluoroacetic acid (1 ml, 10 mmol). After 20 minutes at room temperature, the volatiles were removed under vacuum, and the crude was purified with reverse phase preparative HPLC to give the title compound in a 31% yield.
$^1$H NMR (D$_2$O) δ 7.87 (m, 3H), 7.73 (m, 12H), 3.9 (s, 2H), 3.41 (m, 2H), 3.23 (m, 2H), 2.85 (s, 3H), 1.68 (m, 2H); MS (ESI+) for $C_{25}H_{31}N_4OP$ m/z 433.2 (M$^+$) and MS (ESI+) for $C_{25}H_{31}N_4OP$ m/z 217.2 (M+H)$^{2+}$.

Example 2

Preparation of $N^2$-[ammonio(imino)methyl]-N,$N^2$-dimethyl-N-[3-(triphenylphosphonio)propyl]glycinamide bis(trifluoroacetate)

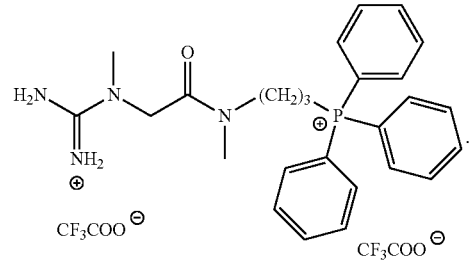

Step 1. Preparation of [3-(methylamino)propyl](triphenyl)phosphonium bromide hydrobromide (3-bromopropyl)(triphenyl)phosphonium bromide (5.7 g, 12 mmol) was treated with 33% methylamine in ethanol (40 mL, 400 mmol) in a sealed tube. The mixture was heated at 100° C. for 1.5 hours and cooled to room temperature. The volatiles were removed, and the resultant semi-solid was taken up in methanol (23 mL) and heated at 50° C., at which point all the solids dissolved. The temperature was lowered to 40° C., and methyl t-butyl ether (68 mL) was added drop wise, giving a slurry. The slurry was cooled to room temperature and filtered, washing the product cake with methyl t-butyl ether (20 mL) to afford the title compound (4.0 g) in a 66% yield as a white solid.

Step 2. Preparation of $N^2$-(tert-butoxycarbonyl)-N,$N^2$-dimethyl-N-[3-(triphenylphosphonio)propyl]glycinamide bromide N-(tert-butoxycarbonyl)-N-methylglycine (309 mg, 1.63 mmol) was taken up in methylene chloride (7.8 mL) and treated with N,N-diisopropylethylamine (1.0 mL, 5.7 mmol), and 1-hydroxybenzotriazole hydrate (233 mg, 1.52 mmol). After 10 minutes at room temperature, [3-(methylamino)propyl](triphenyl)phosphonium bromide hydrobromide (933 mg, 1.88 mmol) was added, followed by 1-ethyl-(3-dimethylaminopropyl)carbodiimide hydrochloride (353 mg, 1.84 mmol) and 4-dimethylaminopyridine (145 mg, 0.11 mmol). The mixture was stirred overnight at room temperature. The reaction was isolated by washing with aqueous NaHCO$_3$ and water to give crude product that was purified on a silica gel column eluting with 5-10% 1 M NH$_3$ in methanol and methylene chloride to give the title compound (739 mg) in a 76% yield.

Step 3. Preparation of N,N$^2$-dimethyl-N-[3-(triphenylphosphonio)propyl]-glycinamide trifluoroacetate N$^2$-(tert-butoxycarbonyl)-N,N$^2$-dimethyl-N-[3-(triphenylphosphonio)propyl]glycinamide bromide (280 mg, 0.48 mmol) was dissolved in trifluoroacetic acid (1.9 mL, 25 mol) at room temperature. After 30 minutes, the volatiles were removed under high vacuum and the crude product taken up in methylene chloride and washed with aqueous NaHCO$_3$. The organic layer was then washed with water and concentrated to give the title compound in quantitative yield.

Step 4. Preparation of N$^2$—{(E)-[(tert-butoxycarbonyl)amino][(tert-butoxycarbonyl)imino]methyl}-N,N$^2$-dimethyl-N-[3-(triphenylphosphonio)propyl] glycinamide trifluoroacetate Di-tert-butyl {[(trifluoromethyl)sulfonyl]carbonimidoyl} biscarbamate (di-Boc-triflylguanidine) (34 mg, 0.087 mmol) was charged to a flame dried flask under nitrogen and treated with anhydrous 1,2-dichloroethane (0.24 mL) and triethyl amine (25 μL, 0.18 mmol). To the reaction was added N,N$^2$-dimethyl-N-[3-(triphenylphosphonio)propyl]glycinamide trifluoroacetate (48 mg, 0.08 mmol) and the mixture was stirred at 50° for 5 hours and cooled to room temperature. The reaction was diluted with methylene chloride and washed with aqueous NaHCO$_3$. The organic layer was concentrated and purified on a silica gel column eluting with 5-20% 1M NH$_3$ in methanol and methylene chloride to give the title compound in a 30% yield.

Step 5. Preparation of N$^2$-[ammonio(imino)methyl]-N,N$^2$-dimethyl-N-[3-(triphenylphosphonio)propyl] glycinamide bis(trifluoroacetate)

N$^2$—{(E)-[(tert-butoxycarbonyl)amino][(tert-butoxycarbonyl)imino]methyl}-N,N$^2$-dimethyl-N-[3-(triphenylphosphonio)propyl]glycinamide trifluoroacetate (330 mg, 0.43 mmol) was dissolved in trifluoroacetic acid (1.6 ml) and stirred at room temperature for 15 minutes, and the crude was isolated upon removal of volatiles. Purification by preparative HPLC to give the title compound as a white solid following lyophilization (18% yield).

$^1$H NMR (DMSO-d$_6$) δ 7.91 (m, 3H), 7.78 (m, 12H), 7.38 (bs, 4H), 4.27 (s, 1.5; H), 4.22 (s, 0.5; H), 3.51 (m, 4H), 2.90 (s, 2.2; H), 2.87 (s, 3H), 2.75 (s, 0.8; H), 1.78 (m, 2H); MS (ESI+) for C$_{26}$H$_{33}$N$_4$OP m/z 224.2 (M+H)$^{2+}$.

Example 3

Preparation of N$^2$-[amino(imino)methyl]-N$^2$-methyl-N-[3-(triphenylphosphonio)-propyl]glycinamide chloride

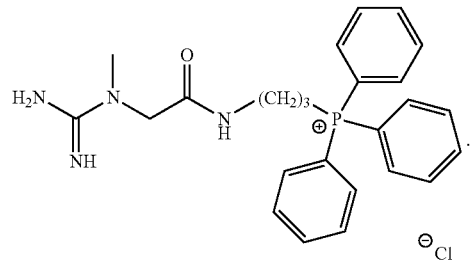

Step 1. Preparation of (3-aminopropyl)(triphenyl)phosphonium dibromide)

To a stirred, degassed solution of 3-bromopropylamine hydrobromide (25.1 g, 115 mmol) in 1-butanol (210 mL) was added triphenylphosphine (42.1 g, 160 mmol). The solution was degassed again by bubbling nitrogen through it for 10 minutes and then heated at 120° C. overnight. The solution was cooled and poured into a stirring solution of methyl t-butyl ether (700 mL) and toluene (400 mL). After stirring at room temperature until a homogenous slurry resulted, the solids were filtered and the product cake rinsed two times with methyl t-butyl ether (2×100 mL) to afford the title compound (54 g, 84%), as a white solid.

$^1$H NMR (DMSO-d$_6$) δ 7.81 (m, 15H), 3.74 (m, 2H), 2.99 (m, 2H), 1.84 (m, 2H).

Step 2. Preparation of N$^2$-(tert-butoxycarbonyl)-N$^2$-methyl-N-[3-(triphenylphosphonio)propyl]glycinamide bromide To a stirred solution of N-(tert-butoxycarbonyl)-N-methylglycine (1.96 g, 10.4 mmol) in N,N-dimethylformamide (9.8 mL) was added N,N-carbonyldiimidazole (1.68 g, 10.4 mmol). After 1 hour at room temperature, (3-aminopropyl)(triphenyl)phosphonium dibromide (5.02 g, 10.4 mmol) was added, and the mixture was stirred overnight at room temperature. The reaction was diluted with methylene chloride (20 mL), and the organic layer was washed with 5 weight percent aqueous lithium chloride (2×10 mL) and 0.5 M citric acid (10 mL). The organic layer was concentrated to give the title compound (4.0 g, 65%) as a white solid.

MS (ESI+) for C$_{29}$H$_{36}$N$_2$O$_3$P m/z 491.4 (M)$^+$.

Step 3. Preparation of N$^2$-(tert-butoxycarbonyl)-N$^2$-methyl-N-[3-(triphenylphosphonio)propyl]glycinamide chloride A solution of N$^2$-(tert-butoxycarbonyl)-N$^2$-methyl-N-[3-(triphenylphosphonio)propyl]glycinamide bromide (53.7 g, 93.9 mmole) in methylene chloride (450 mL) was stirred with 20 weight percent aqueous lithium chloride containing 2 weight percent tetrabutylammonium chloride (4×150 mL/g). The organic layer was concentrated to dryness give the title compound in quantitative yield.

MS (ESI+) for C$_{29}$H$_{36}$N$_2$O$_3$P m/z 491.4 (M)$^+$.

Step 4. Preparation of N$^2$-methyl-N-[3-(triphenylphosphonio)propyl]glycinamide chloride To a solution of N$^2$-(tert-butoxycarbonyl)-N$^2$-methyl-N-[3-(triphenylphosphonio)propyl]glycinamide chloride (7.6 g, 14 mol) in methylene chloride (38 mL) and methanol (4.2 mL) was added 2.0 M HCl in diethyl ether (16 mL, 32 mmol), and the mixture was stirred overnight at room temperature. The solution was cooled to 0° C. and treated with 7 M ammonia in methanol (6.0 mL, 42 mmol), giving an immediate white precipitate. After 30 minutes, the slurry was filtered and the flask and filter cake were rinsed with methylene chloride (68 mL). The filtrate was concentrated to give the title compound (6.2 g, 100%) as a crude white solid.

$^1$H NMR (DMSO-$d_6$) δ 7.69 (m, 15H), 3.81 (s, 2H), 3.35 (m, 2H), 3.27 (m, 2H), 1.86 (m, 2H).

Step 5. Preparation of $N^2$-[amino(imino)methyl]-$N^2$-methyl-N-[3-(triphenylphosphonio)-propyl]glycinamide chloride To a solution of $N^2$-methyl-N-[3-(triphenylphosphonio) propyl]glycinamide chloride (7.65 g, 17.9 mmol) in N,N-dimethylformamide (15 mL) was added 1-H-pyrazole-1-carboximidamide hydrochloride (2.76 g, 18.8 mmol) and N,N-diisopropylethylamine (3.28 mL, 18.8 mmol). The mixture was stirred overnight at room temperature. After stirring overnight, the reaction was not complete, and additional 1-H-pyrazole-1-carboximidamide hydrochloride (394 mg, 2.69 mmol) and N,N-diisopropylethylamine (0.47 mL, 2.69 mmol) were added. After 8 hours, additional 1-H-pyrazole-1-carboximidamide hydrochloride (338 mg, 2.3 mmol) and N,N-Diisopropylethylamine (0.40 mL, 2.3 mmol) were added again. The mixture was stirred overnight again. The reaction was diluted with methylene chloride (30 mL), and then the solution was added to a flask containing a rapidly stirring mixture of methylene chloride (15 mL) and methyl t-butyl ether (61 mL) to precipitate the product. The supernatant was decanted, and the product was dried under high vacuum at 35° C. to give the title compound (9.4 g, 100% yield about 80% pure) as a crude light yellow solid.

$^1$H NMR (D$_2$O) δ 7.67 (m, 15H), 4.00 (s, 2H), 3.27 (m, 2H), 3.19 (m, 2H), 2.88 (s, 3H), 1.83 (m, 2H).

Step 6. Crystallization of $N^2$-[amino(imino)methyl]-$N^2$-methyl-N-[3-(triphenylphosphonio)-propyl]glycinamide chloride $N^2$-[amino(imino)methyl]-$N^2$-methyl-N-[3-(triphenylphosphonio)propyl]glycinamide chloride (10.1 g, 17.9 mmol) was dissolved in methylene chloride (40 mL) and stirred at room temperature for 24 hours to give a slurry of white solids. The solids were filtered and dried to give the title compound (3.6 g, 43% yield, >95% pure).

$^1$H NMR (D$_2$O) δ 7.67 (m, 15H), 4.00 (s, 2H), 3.27 (m, 2H), 3.19 (m, 2H), 2.88 (s, 3H), 1.83 (m, 2H); MS (ESI+) for C$_{25}$H$_{30}$N$_4$OP m/z 433.3 (M)$^+$.

Example 4

Preparation of $N^2$-[ammonio(imino)methyl]-$N^2$-methyl-N-[3-(triphenylphosphonio)propyl]glycinamide dichloride

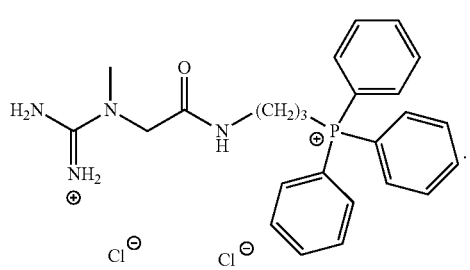

Modified creatine compound of example 4 was prepared from the product of example 3 using the synthetic methodology described below.

$N^2$-[ammonio(imino)methyl]-$N^2$-methyl-N-[3-(triphenylphosphonio)propyl]glycinamide bis(trifluoroacetate) (100 mg, 0.15 mmol) was dissolved in excess methanolic hydrochloride, and the volatiles were removed to give the title compound (75 mg) in a quantitative yield.

$^1$H NMR (D$_2$O) δ 7.89 (m, 3H), 7.76 (m, 12H), 3.99 (s, 2H), 3.52 (m, 2H), 3.25 (m, 2H), 2.87 (s, 3H), 1.68 (m, 2H); MS (ESI+) for C$_{25}$H$_{31}$N$_4$OP m/z 433.2 (M$^+$) and MS (ESI+) for C$_{25}$H$_{31}$N$_4$OP m/z 217.2 (M+H)$^{2+}$.

Example 5

Preparation of $N^3$-[ammonio(imino)methyl]-$N^3$-methyl-N-[4-(triphenylphosphonio)butyl]-O-alaninamide bis(trifluoroacetate)

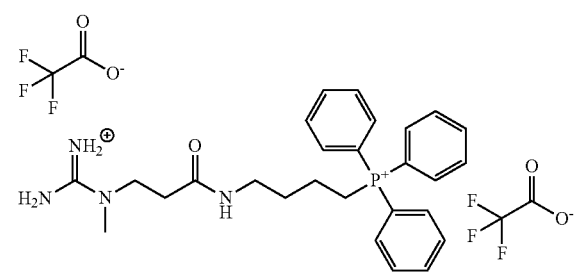 [SMILES: O=C([O-])C(F)(F)F ; CN(CCC(=O)NCCCC[P+](c1ccccc1)(c1ccccc1)c1ccccc1)C(N)=[NH2+] ; O=C([O-])C(F)(F)F]

Step 1. Preparation of $N^3$-(tert-butoxycarbonyl)-$N^3$-methyl-N-[4-(triphenylphosphonio)butyl]-β-alaninamide bromide N-(tert-butoxycarbonyl)-N-methyl-β-alanine (Matrix Scientific, 368 mg, 1.81 mmol) was dissolved in N,N-dimethylformamide (3.7 mL) and treated with N,N-carbonyldiimidazole (308 mg, 1.90 mmol). The reaction mixture was stirred at room temperature for 30 minutes. (4-Aminobutyl)(triphenyl)phosphonium bromide (1.12 g, 2.72 mmol) was added, and the reaction was stirred overnight at room temperature. The reaction was then diluted with methylene chloride and washed with 5% aqueous lithium chloride (3 times), 1N aqueous hydrogen chloride, and saturated sodium bicarbonate. The organic solution was dried over anhydrous sodium sulfate, filtered, and concentrated to give the title compound (1.26 g, 100%, 86% pure) as a white foam. Sample was used crude in next step.

$^1$H NMR (DMSO-$d_6$) δ 7.85 (m, 16H), 3.58 (m, 2H), 3.28 (m, 2H), 3.07 (m, 2H) 2.72 (bs, 3H), 2.20 (m, 2H), 1.57 (m, 4H), 1.37 (bs, 9H). MS (ESI+) for C$_{31}$H$_{40}$N$_2$O$_3$P m/z 519.4 (M)$^+$.

Step 2. Preparation of $N^3$-methyl-N-[4-(triphenylphosphonio)butyl]-β-alaninamide bromide $N^3$-(tert-butoxycarbonyl)-$N^3$-methyl-N-[4-(triphenylphosphonio)butyl]-β-alaninamide bromide (1.08 g, 1.80 mmol) was dissolved in methylene chloride (5.4 mL) and methanol (0.54 mL). The solution at room temperature was treated with 2.0 M hydrogen chloride in diethyl ether (1.98 mL, 3.96 mmol). The mixture was stirred overnight at room temperature, then cooled with an ice bath and treated with 7N ammonia in methanol (0.75 mL, 5.22 mmol). After 30 minutes, the resulting slurry was filtered, and the solids were washed with methylene chloride. The filtrate was concentrated to give the title compound (980 mg, 110%, 84% pure) as a white foam. The product of step 2 was used crude in the next step.

$^1$H NMR (DMSO-$d_6$) δ 7.91 (m, 17H), 3.58 (m, 2H), 3.07 (m, 2H) 2.66 (m, 2H), 2.27 (s, 3H), 2.20 (m, 2H), 1.57 (m, 4H). MS (ESI+) for $C_{26}H_{52}N_2OP$ m/z 419.3 (M)$^+$.

Step 3. Preparation of $N^3$-[amino(imino)methyl]-$N^3$-methyl-N-[4-(triphenylphosphonio)butyl]-β-alaninamide bromide $N^3$-methyl-N-[4-(triphenylphosphonio)butyl]-β-alaninamide bromide (980 mg, 2.0 mmol) was dissolved in N,N-dimethylformamide (2 mL). The resultant solution was treated with 1H-pyrazole-1-carboximidamide hydrochloride (315 mg, 2.15 mmol) and N,N-diisopropylethylamine (0.39 mL, 2.26 mmol). The reaction was stirred overnight at room temperature. More 1H-pyrazole-1-carboximidamide hydrochloride and N,N-diisopropylethylamine can be added to effect further conversion. The reaction mixture in N,N-dimethylformamide was used without work-up in the next step.

Step 4. Preparation of $N^3$-[amino(imino)methyl]-$N^3$-methyl-N-[4-(triphenylphosphonio)butyl]-β-alaninamide trifluoroacetate-trifluoroacetic acid (1:1)

$N^3$-[amino(imino)methyl]-$N^3$-methyl-N-[4-(triphenylphosphonio)butyl]-β-alaninamide bromide as a solution in N,N-dimethylformamide was purified directly on a C18 column eluting with a gradient of water (with 0.1% TFA) and acetonitrile (with 0.07% TFA) to isolate $N^3$-[amino(imino)methyl]-$N^3$-methyl-N-[4-(triphenylphosphonio)butyl]-β-alaninamide trifluoroacetate-trifluoroacetic acid (1:1) (800 mg) in a 60% purified yield.

$^1$H NMR (DMSO-$d_6$ with $D_2O$) δ 7.85 (m, 15H), 3.55 (m, 2H), 3.46 (b, 2H), 3.08 (m, 2H), 2.86 (s, 3H), 2.34 (m, 2H), 1.57 (m, 4H). MS (ESI+) for $C_{27}H_{34}N_4OP$ m/z 461.2 (M)$^+$.

Example 6

Preparation of {4-[(4-{[ammonio(imino)methyl](methyl)amino}butanoyl)amino]butyl}(triphenyl)phosphonium bis(trifluoroacetate)

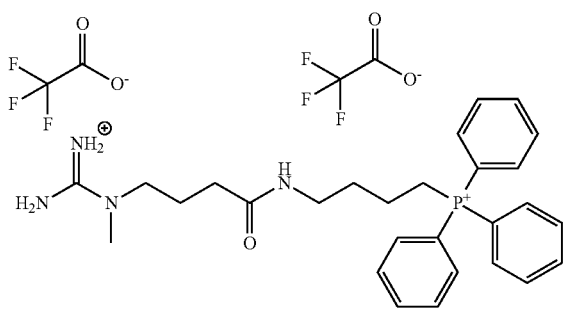 [SMILES: O=C([O-])C(F)(F)F ; CN(CCCC(=O)NCCCC[P+](c1ccccc1)(c1ccccc1)c1ccccc1)C(N)=[NH2+] ; O=C([O-])C(F)(F)F]

Step 1. Preparation of 11,14,14-trimethyl-7,12-dioxo-1,1,1-triphenyl-13-oxa-6,11-diaza-1-phosphoniapentadecane bromide 4-[(tert-butoxycarbonyl)(methyl)amino]butanoic acid (*J. Organic Chemistry*, 1985, 50, 1302-1304, 349 mg, 1.61 mol) was dissolved in N,N-dimethylformamide (3.5 mL) and treated with N,N-carbonyldiimidazole (273 mg, 1.69 mmol). The mixture was stirred at room temperature for 30 minutes. (4-Aminobutyl)(triphenyl)phosphonium bromide (929 mg, 1.40 mmol) was added, and the reaction was stirred overnight at room temperature. The reaction mixture was diluted with methylene chloride and washed with 5% aqueous lithium chloride (3 times), 1N aqueous hydrogen chloride, and saturated sodium bicarbonate. The organic solution was dried over anhydrous sodium sulfate, filtered, and concentrated to give the title compound (0.91 g, 92%, 83% pure) as a white foam. Sample was used crude in next step.

$^1$H NMR (DMSO-$d_6$) δ 7.81 (m, 16H), 3.55 (m, 2H), 3.07 (m, 4H), 2.72 (s, 3H), 1.94 (m, 2H), 1.57 (m, 6H), 1.37 (s, 9H). MS (ESI+) for $C_{32}H_{42}N_2O_3P$ m/z 534.4 (M)$^+$.

Step 2. Preparation of (4-{[4-(methylamino)butanoyl]amino}butyl)(triphenyl)phosphonium bromide 11,14,14-trimethyl-7,12-dioxo-1,1,1-triphenyl-13-oxa-6,11-diaza-1-phosphoniapentadecane bromide (910 mg, 1.50 mmol) was dissolved in methylene chloride (4.6 mL) and methanol (0.50 mL). The solution at room temperature was treated with 2.0 M hydrogen chloride in diethyl ether (1.63 mL, 3.26 mmol). The mixture was stirred overnight at room temperature, then cooled with an ice bath and treated with 7N ammonia in methanol (0.61 mL, 4.30 mmol). After 30 minutes, the slurry that resulted was filtered, and the solids were washed with methylene chloride. The filtrate was concentrated to give the title compound (690 mg, 91%, 91% pure) as a white foam. The product of step 2 was used crude in next step.

$^1$H NMR (DMSO-$d_6$) δ 7.81 (m, 17H), 3.58 (m, 2H), 3.06 (m, 2H), 2.39 (m, 2H), 2.32 (s, 3H), 2.01 (m, 2H), 1.54 (m, 6H). MS (ESI+) for $C_{27}H_{34}N_2OP$ m/z 433.3 (M)$^+$.

Step 3. Preparation of {4-[(4-{[amino(imino)methyl](methyl)amino}butanoyl)amino]butyl}(triphenyl)phosphonium bromide (4-{[4-(methylamino)butanoyl]amino}butyl)(triphenyl)phosphonium bromide (690 mg, 1.30 mmol) was dissolved in N,N-dimethylformamide (1.4 mL). The resultant solution was treated with 1H-pyrazole-1-carboximidamide hydrochloride (216 mg, 1.47 mmol) and N,N-diisopropylethylamine (0.27 mL, 1.54 mmol). The reaction was stirred overnight at room temperature. More 1H-pyrazole-1-carboximidamide hydrochloride and N,N-diisopropylethylamine can be added to effect further conversion. The reaction mixture in N,N-dimethylformamide was used in the purification without isolation.

Step 4. Preparation of {4-[(4-{[amino(imino)methyl](methyl)amino}butanoyl)amino]butyl}(triphenyl)phosphonium trifluoroacetate-trifluoroacetic acid (1:1)

$N^3$-[amino(imino)methyl]-$N^3$-methyl-N-[4-(triphenylphosphonio)butyl]-β-alaninamide bromide as a solution in N,N-dimethylformamide was purified directly on a C18 column eluting with a gradient of water (with 0.1% TFA) and acetonitrile (with 0.07% TFA) to isolate the title compound (630 mg) in a 67% purified yield.

$^1$H NMR (DMSO-$d_6$ with $D_2O$) δ 7.83 (m, 15H), 3.58 (m, 2H), 3.20 (m, 2H), 3.08 (m, 2H), 2.91 (3, 3 H), 2.03 (m, 2H), 1.61 (m, 6H). MS (ESI+) for $C_2H_{36}N_4OP$ m/z 475.2 (M)$^+$.

Example 7

Preparation of {4-[(4-{[ammonio(imino)methyl](methyl)amino}-2,2-dimethylbutanoyl)amino]butyl}(triphenyl)phosphonium bis(trifluoroacetate)

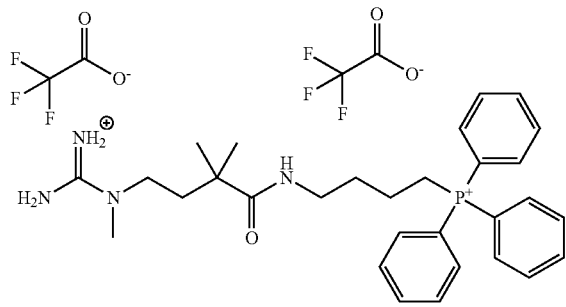 [SMILES: O=C([O-])C(F)(F)F ; CN(CCC(C)(C)C(=O)NCCCC[P+](c1ccccc1)(c1ccccc1)c1ccccc1)C(N)=[NH2+] ; O=C([O-])C(F)(F)F]

Step 1. Preparation of 8,8,11,14,14-pentamethyl-7,12-dioxo-1,1,1-triphenyl-13-oxa-6,11-diaza-1-phosphoniapentadecane bromide 4-[(tert-butoxycarbonyl)(methyl)amino]-2,2-dimethylbutanoic acid (Organic and Molecular Chemistry, 2011, 9, 1846-1854, 117 mg, 0.48 mmol) was dissolved in N,N-dimethylformamide (1.2 mL) and treated with N,N-carbonyldiimidazole (104 mg, 0.64 mmol). The mixture was stirred at room temperature for 30 minutes. (4-Aminobutyl)(triphenyl)phosphonium bromide (277 mg, 0.67 mmol) was added, and the reaction was stirred overnight at room temperature. The reaction mixture was then diluted with methylene chloride and washed with 5% aqueous lithium chloride (3 times), 1N aqueous hydrogen chloride, and saturated sodium bicarbonate. The organic solution was dried over anhydrous sodium sulfate, filtered, and concentrated to give the title compound (210 mg, 69%) as a white foam. Sample was used crude in next step.

MS (ESI+) for $C_{34}H_{46}N_2O_3P$ m/z 561.5 (M)$^+$.

Step 2. Preparation of (4-{[2,2-dimethyl-4-(methylamino)butanoyl]amino}butyl)(triphenyl)phosphonium bromide 8,8,11,14,14-pentamethyl-7,12-dioxo-1,1,1-triphenyl-13-oxa-6,11-diaza-1-phosphoniapentadecane bromide (205 mg, 0.32 mmol) was dissolved in methylene chloride (1.0 mL) and methanol (0.10 mL). The solution at room temperature was treated with 2.0 M hydrogen chloride in diethyl ether (0.36 mL, 0.71 mmol). The reaction was stirred overnight at room temperature, cooled with an ice bath, and treated with 7N ammonia in methanol (0.13 mL, 0.93 mmol). After 30 minutes, the slurry that resulted was filtered, and the solids were washed with methylene chloride. The filtrate was concentrated to give the title compound (170 mg, 98%) as a white foam. The product of step 2 was used crude in next step.

MS (ESI+) for $C_{29}H_{38}N_2OP$ m/z 460.9 (M)$^+$.

Step 3. Preparation of {4-[(4-{[amino(imino)methyl](methyl)amino}-2,2-dimethylbutanoyl)amino]butyl}(triphenyl)phosphonium bromide (4-{[2,2-dimethyl-4-(methylamino)butanoyl]amino}butyl)(triphenyl)phosphonium bromide (171 mg, 0.32 mmol) was dissolved in N,N-dimethylformamide (0.34 mL). The resultant solution was treated with 1H-pyrazole-1-carboximidamide hydrochloride (65 mg, 0.44 mmol) and N,N-diisopropylethylamine (0.083 mL, 0.47 mmol). The reaction was stirred overnight at room temperature. More 1H-pyrazole-1-carboximidamide hydrochloride and N,N-diisopropylethylamine can be added to effect further conversion. The reaction mixture in N,N-dimethylformamide was used in the purification without isolation.

Step 4. Preparation of {4-[(4-{[amino(imino)methyl](methyl)amino}-2,2-dimethylbutanoyl)amino]butyl}(triphenyl)phosphonium trifluoroacetate-trifluoroacetic acid (1:1)

$N^3$-[amino(imino)methyl]-$N^3$-methyl-N-[4-(triphenylphosphonio)butyl]-β-alaninamide bromide as a solution in N,N-dimethylformamide was purified directly on a C18 column eluting with a gradient of water (with 0.1% TFA) and acetonitrile (with 0.07% TFA) to isolate {4-[(4-{[amino(imino)methyl](methyl)amino}butanoyl)amino]butyl}(triphenyl)phosphonium trifluoroacetate-trifluoroacetic acid (1:1) (99 mg, 43%).

$^1$H NMR (DMSO-d$_6$ with D$_2$O) δ 7.83 (m, 17H), 3.56 (m, 2H), 3.07 (m, 4H), 2.91 (s, 3H), 1.61 (m, 4H), 1.49 (m, 2H), 1.00 (s, 6H). MS (ESI+) for $C_{30}H_{40}N_4OP$ m/z 503.1 (M)$^+$.

Example 8

Preparation of [3-({[1-({[ammonio(imino)methyl](methyl)amino}methyl)cyclopropyl]carbonyl}amino)propyl](triphenyl)phosphonium bis(trifluoroacetate)

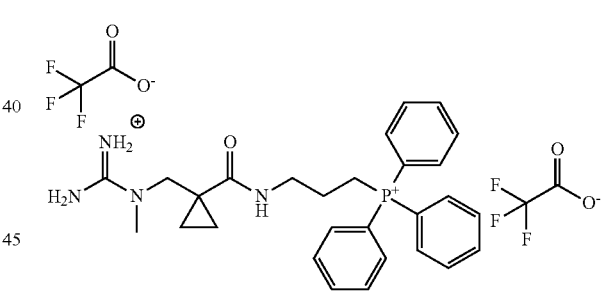

Step 1. Preparation of methyl 1-{[[(tert-butoxycarbonyl)(methyl)amino]methyl}cyclopropanecarboxylate 1-{[(tert-butoxycarbonyl)amino]methyl}cyclopropane carboxylic acid (Chem-Impex International, Inc., 682 mg, 3.17 mmol) was dissolved in N,N-dimethylformamide (6.8 mL) and cooled with an ice bath. To the solution was added sodium hydride, 60% in mineral oil (279 mg, 6.97 mmol). After 30 minutes, the mixture was treated with methyl iodide (0.592 mL, 9.5 mmol) and warmed to room temperature. After 2 hours, the reaction was poured into a cold (ice bath temperature) mixture of 1N aqueous hydrogen chloride (13.9 mL) and saturated sodium chloride (13.9 mL). The product was extracted with ethyl acetate (3 times). Concentration of the organic layers gives the title compound (1.1 g), which was used directly in the next step.

MS (ESI+) for $C_{12}H_{21}NO_4$ m/z 266.1 (M+Na)$^+$.

Step 2. Preparation of 1-{[(tert-butoxycarbonyl)(methyl)amino]methyl}cyclopropanecarboxylic acid Methyl 1-{[(tert-butoxycarbonyl)(methyl)amino]methyl}cyclopropanecarboxylate was dissolved in methanol (6.8 mL) and water (5.8 mL) and treated with 10M sodium hydroxide (0.98 mL, 9.82 mmol). The solution was heated at 50° C. After 30 minutes, the reaction was cooled with an ice bath and quenched into a cold (ice bath temperature) mixture of 1N hydrogen chloride (19.6 mL) and saturated sodium chloride (19.6 mL). The product was extracted with ethyl acetate (3 times). The organic solution was dried over anhydrous sodium sulfate and filtered. Concentration of the organic solution gave the title compound (680 mg, 94% yield) which was used crude in the next step.

MS (ESI−) for $C_{11}H_{19}NO_4$ m/z 228.3 (M−H)⁻.

Step 3. Preparation of (3-{[(1-{[(tert-butoxycarbonyl)(methyl)amino]methyl}cyclopropyl)carbonyl]amino}propyl)(triphenyl)phosphonium bromide 1-{[(tert-butoxycarbonyl)(methyl)amino]methyl}cyclopropanecarboxylic acid (680 mg, 3.0 mmol) was dissolved in N,N-dimethylformamide (6.8 mL) and treated with N,N-carbonyldiimidazole (571 mg, 3.52 mmol). The mixture was stirred at room temperature for 30 minutes. To the solution was added (3-ammoniopropyl)(triphenyl)phosphonium dibromide (1.93 g, 4.00 mmol). The mixture was stirred overnight at room temperature and then diluted with methylene chloride and washed with 5% aqueous lithium chloride (3 times), 1N aqueous hydrogen chloride, and saturated sodium bicarbonate. The organic solution was dried over anhydrous sodium sulfate, filtered, and concentrated to give crude title compound. The crude product was purified on a silica gel column eluting with a gradient of 0-20% methanol with methylene chloride to isolate the title compound (810 mg, 40%, 91% pure).

MS (ESI+) for $C_{32}H_{40}N_2O_3P$ m/z 531.5 (M)⁺.

Step 4. Preparation of {3-[({1-[(methylamino)methyl]cyclopropyl}carbonyl)amino]propyl}(triphenyl)phosphonium bromide (3-{[(1-{[(tert-butoxycarbonyl)(methyl)amino]methyl}cyclopropyl)carbonyl]amino}-propyl)(triphenyl)phosphonium bromide (809 mg, 1.32 mmol) was dissolved in methylene chloride (4.0 mL) and methanol (0.4 mL). The solution at room temperature was treated with 2.0 M hydrogen chloride in diethyl ether (1.7 mL, 3.44 mmol). The mixture was stirred overnight at room temperature. To the incomplete reaction was added additional 2.0 M hydrogen chloride in diethyl ether (0.36 mL, 0.71 mmol). After 3 additional hours, the reaction mixture was cooled with an ice bath and treated with 7N ammonia in methanol (0.77 mL, 5.42 mmol). After 30 minutes, the slurry that resulted was filtered, and the solids were washed with methylene chloride. The filtrate was concentrated to give the title compound (760 mg, 110%, 85% pure). The product of step 4 was used crude in next step.

MS (ESI+) for $C_{27}H_{32}N_2OP$ m/z 431.2 (M)⁺.

Step 5. Preparation of [3-({[1-({[amino(imino)methyl](methyl)amino}methyl)cyclopropyl]carbonyl}amino)propyl](triphenyl)phosphonium bromide {3-[({1-[(methylamino)methyl]cyclopropyl}carbonyl)amino]propyl}(triphenyl)-phosphonium bromide (229 mg, 0.45 mmol) was dissolved in N,N-dimethylformamide (0.46 mL). The resultant solution was treated with 1H-pyrazole-1-carboximidamide hydrochloride (92 mg, 1.4 mmol) and N,N-diisopropylethylamine (0.12 mL, 0.67 mmol). The reaction was stirred overnight at room temperature. Additional 1H-pyrazole-1-carboximidamide hydrochloride and N,N-diisopropylethylamine can be added to the reaction to effect further conversion. The reaction mixture in N,N-dimethylformamide was used in the purification without isolation.

Step 6. Preparation of [3-({[1-({[amino(imino)methyl](methyl)amino}methyl)cyclopropyl]carbonyl}amino)propyl](triphenyl)phosphonium trifluoroacetate-trifluoroacetic acid (1:1)

[3-({[1-({[amino(imino)methyl](methyl)amino}methyl)cyclopropyl]carbonyl}amino)-propyl](triphenyl)phosphonium bromide as a solution in N,N-dimethylformamide was purified directly on a C18 column eluting with a gradient of water (with 0.1% TFA) and acetonitrile (with 0.07% TFA) to isolate [3-({[1-({[amino(imino)methyl](methyl)amino}methyl)cyclopropyl]-carbonyl}amino)propyl](triphenyl)phosphonium trifluoroacetate-trifluoroacetic acid (1:1) (144 mg, 46% yield).

¹H NMR (DMSO-d₆ with D₂O) δ 7.83 (m, 16H), 3.50 (m, 4H), 3.17 (m, 2H), 2.86 (s, 3H), 1.62 (m, 2H), 1.11 (m, 2H), 0.88 (m, 2H). MS (ESI+) for $C_{28}H_{34}N_4OP$ m/z 473.1

Example 9

Preparation of [3-({[4-({[ammonio(imino)methyl](methyl)amino}methyl)tetrahydro-2H-pyran-4-yl]carbonyl}amino)propyl](triphenyl)phosphonium bis(trifluoroacetate)

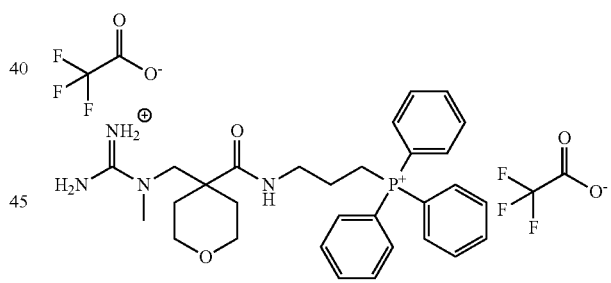

Step 1. Preparation of 4-{[(tert-butoxycarbonyl)amino]methyl}tetrahydro-2H-pyran-4-carboxylic acid 4-Aminomethyltetrahydropyran-4-carboxylic acid (AstaTech, Inc., 478 mg, 3.00 mmol) was dissolved in 1,4-dioxane (8.5 mL) and water (4.2 mL). To the solution was added potassium carbonate (664 mg, 4.80 mmol) and di-tert-butyldicarbonate (918 mg, 4.20 mmol). After stirring at room temperature overnight, the reaction was diluted with water and washed with ethyl acetate (2 times). The aqueous layer was then acidified with 1 N aqueous hydrochloric acid, and the product was extracted with ethyl acetate (3 times). Concentration of the organic layers the title compound (729 mg, 94% yield). The sample was used directly in the next step.

MS (ESI−) for $C_{12}H_{21}NO_5$ m/z 258.3 (M−H)⁻.

Step 2. Preparation of methyl 4-{[(tert-butoxycarbonyl)(methyl)amino]methyl}tetrahydro-2H-pyran-4-carboxylate 4-{[(tert-Butoxycarbonyl)amino]methyl}tetrahydro-2H-pyran-4-carboxylic acid (729 mg, 2.81 mmol) was dissolved in N,N-dimethylformamide (7.3 mL) and cooled with an ice bath. To the solution was added sodium hydride, 60% in mineral oil (337 mg, 8.43 mmol), and the solution was warmed to room temperature. Dimethyl sulfate (612 µL, 6.47 mmol) was added, and the mixture was heated at 50° C. After 30 minutes, the reaction was cooled to room temperature, and additional 60% sodium hydride in mineral oil (56.2 mg, 1.40 mmol) and dimethyl sulfate (133 µL, 1.40 mmol) were added: The mixture was then heated at 50° C. for 1 hour. The reaction was cooled with an ice bath and quenched into a cold (ice bath temperature) mixture of 1 N hydrogen chloride (19.7 mL) and saturated sodium chloride (19.7 mL). The product was extracted with ethyl acetate (3 times). The organic solution was dried over anhydrous sodium sulfate and filtered. Concentration of the organic solution gave the title compound, which was used crude in the next step.
MS (ESI+) for $C_{14}H_{25}NO_5$ m/z 288.2 (M+H)$^+$.

Step 3. Preparation of 4-{[(tert-butoxycarbonyl)(methyl)amino]methyl}tetrahydro-2H-pyran-4-carboxylic acid Methyl 4-{[(tert-butoxycarbonyl)(methyl)amino]methyl}tetrahydro-2H-pyran-4-carboxylate (2.81 mmol) was dissolved in methanol (7.3 mL) and water (5.9 mL) and treated with 10 M sodium hydroxide (1.40 mL, 14.0 mmol). The solution was heated at 60° C. overnight. The reaction was cooled to room temperature, and volatiles were removed on a rotovap. The remaining solution was diluted with water and washed with ethyl acetate (2 times). The water layer was cooled with an ice bath and then acidified with a mixture of 1 N aqueous HCl (28.1 mL) and saturated sodium chloride (28.1 mL). The product was extracted with ethyl acetate (3 times), and the organic solution was dried over anhydrous sodium sulfate and filtered. Concentration of the organic solution gave the title compound (750 mg, 97% yield) which was used crude in the next step.
$^1$H NMR (DMSO-d$_6$) δ 3.89 (m, 2H), 3.48 (m, 4H), 2.90 (s, 3H), 2.07 (m, 2H), 1.62 (m, 2H), 1.46 (s, 9H); MS (ESI–) for $C_{13}H_{23}NO_5$ m/z 272.4 (M–H)$^-$.

Step 4. Preparation of (3-{[(4-{[(tert-butoxycarbonyl)(methyl)amino]methyl}-tetrahydro-2H-pyran-4-yl)carbonyl]amino}propyl)(triphenyl)phosphonium bromide 4-{[(tert-Butoxycarbonyl)(methyl)amino]methyl}tetrahydro-2H-pyran-4-carboxylic acid (549 mg, 2.01 mmol) was dissolved in N,N-dimethylformamide (5.5 mL). To this solution were added N,N-diisopropylethylamine (385 µL, 2.21 mmol), 1-hydroxybenzotriazole hydrate (323 mg, 2.11 mmol), N-(3-dimethylaminopropyl)-N'-ethylcarbodiimide hydrochloride (578 mg, 3.01 mmol), and (3-ammoniopropyl)(triphenyl)phosphonium dibromide (1.16 g, 2.41 mmol). The reaction mixture was stirred overnight at room temperature, then diluted with methylene chloride and washed with 5% aqueous lithium chloride (3 times), 1N aqueous hydrogen chloride, and saturated sodium bicarbonate. The organic solution was dried over anhydrous sodium sulfate, filtered, and concentrated to give crude the title compound. The crude product was purified on a silica gel column eluting with 10% methanol with methylene chloride to isolate the title compound (729 mg, 55.4% yield).
MS (ESI+) for $C_{34}H_{44}N_2O_4P$ m/z 575.5 (M)$^+$.

Step 5. Preparation of (3-{[(4-{[(tert-butoxycarbonyl)(methyl)amino]methyl}-tetrahydro-2H-pyran-4-yl)carbonyl]amino}propyl)(triphenyl)phosphonium bromide (3-{[(4-{[(tert-Butoxycarbonyl)(methyl)amino]methyl}tetrahydro-2H-pyran-4-yl)carbonyl]amino}propyl)(triphenyl)phosphonium bromide (83 mg, 0.13 mmol) was dissolved in methylene chloride (0.42 mL) and methanol (42 µL). To the solution at room temperature was added 2.0 M hydrogen chloride in diethyl ether (158 mL, 0.32 mmol). The mixture was stirred overnight at room temperature. If the reaction is not complete, additional 2.0 M hydrogen chloride in diethyl ether can be added. The reaction was cooled with an ice bath and treated with 7 N ammonia in methanol (70 µL, 0.49 mmol). After 30 minutes, the slurry that resulted was filtered, and the solids were washed with methylene chloride. The filtrate was concentrated to give the title compound (70 mg), which was used crude in next step.
MS (ESI+) for $C_{29}H_{36}N_2O_2P$ m/z 475.3 (M)$^+$.

Step 6. Preparation of [3-({[4-({[amino(imino)methyl](methyl)amino}methyl)tetrahydro-2H-pyran-4-yl]carbonyl}amino)propyl](triphenyl)phosphonium bromide (3-{[(4-{[(tert-Butoxycarbonyl)(methyl)amino]methyl}tetrahydro-2H-pyran-4-yl)carbonyl]amino}propyl)(triphenyl)phosphonium bromide (71 mg, 0.13 mmol) was dissolved in N,N-dimethylformamide (140 µL). To the resulting solution was added 1H-pyrazole-1-carboximidamide hydrochloride (22 mg, 0.15 mmol) and N,N-diisopropylethylamine (29 µL, 0.17 mmol). The reaction was stirred overnight at room temperature. Additional 1H-pyrazole-1-carboximidamide hydrochloride and N,N-diisopropylethylamine can be added to the reaction if it is not complete. The reaction mixture in N,N-dimethylformamide was used in the purification without isolation.

Step 7. Preparation of [3-({[4-({[amino(imino)methyl](methyl)amino}methyl)tetrahydro-2H-pyran-4-yl]carbonyl}amino)propyl](triphenyl)phosphonium trifluoroacetate-trifluoroacetic acid (1:1)

[3-({[4-({[Amino(imino)methyl](methyl)amino}methyl)tetrahydro-2H-pyran-4-yl]carbonyl}amino)propyl](triphenyl)phosphonium bromide as a solution in N,N-dimethylformamide was purified directly on a C18 column eluting with a gradient of water (with 0.1% TFA) and acetonitrile (with 0.07% TFA) to isolate the title compound (1:1) (3 mg, 3.1% yield).
$^1$H NMR (DMSO-d$_6$ with D$_2$O) δ 7.74 (m, 16H), 3.67 (m, 2H), 3.53 (m, 4H), 3.26 (m, 2H), 3.12 (m, 2H), 2.76 (s, 3H), 1.91 (m, 2H), 1.71 (m, 2H), 1.48 (m, 2H). MS (ESI+) for $C_{30}H_{38}N_4O_2P$ m/z 517.0 (M)$^+$.

Biological Activities

Example 1

Determination of CPK Activity

An in vitro assay was performed to determine the activity of recombinant CPK on the modified creatine compounds (CK, Native Human Creatine Kinase from Cell Sciences Catalog No: CSI14786B). Recombinant CPK (10 units/well) is mixed with 1 mM ATP and the compound of example 1 (compound 1) at varying concentrations (5 mM, 2.5 mM, and 1 mM) or creatine (5 mM). ATP hydrolysis; a measure of the rate of transfer of the gamma phosphate from ATP to the guanidinium groups of the creatine subunit was then measured for each sample using luciferase. Luciferase is then added (GLO kit from Promega) according to manufacturer instructions. As ATP is consumed, light is emitted. Every 2 minutes we collected the emitted light in our plate reader in lumens. The data is collected over 30 minutes to generate a slope. The slope is a measure of ATP consumption. A more negative slope indicates a greater transfer of ATP by CK (CPK) to creatine or the compound of example 1. The rate of ATP hydrolysis/consumption for the compound of example 1 was compared to the rate of ATP hydrolysis/consumption for creatine (5 mM).

The results of the assay are shown in FIG. 1. Addition of creatine caused an increase in ATP hydrolysis/consumption as expected. Upon addition of an equimolar concentration of compound 1 ("Mito-Creatine"), a higher rate of ATP hydrolysis/consumption relative to creatine was observed, suggesting improved activity on CPK.

Example 2

Analysis of Oxygen Consumption Rate (OCR)

The effects of creatine compounds of interest on mitochondrial bioenergetics was assessed by determining their effect on cellular OCR.

In this assay, an XF24 extracellular flux analyzer (Seahorse Bioscience, North Billerica, Mass.) was used to measure mitochondrial oxygen consumption in intact cells. The XF24 analyzer creates a transient 7 µl chamber in specialized microplates that allows determination of oxygen and proton concentrations in real time through the measurement of oxygen sensitive dyes by the XF24 instrument. 24 hours prior to OCR measurement, fibroblasts were seeded into 20 wells of the 24 well tissue culture plate while 1 ml of XF Calibrant solution (Seahorse Bioscience, North Billerica, Mass.) was added to each well of a 24 well dual-analyte sensor cartridge (Seahorse Bioscience, North Billerica, Mass.). The sensor cartridge repositioned on the 24 well calibration plate, and the plate was incubated overnight at 37° C. without additional $CO_2$.

The day of the experiment, the injection ports on the sensor cartridge were loaded with compound 1 or creatine as indicated at 10× concentrations and placed into the XF24 Flux Analyzer for automated calibration. During the sensor calibration, cells in each of the tissue culture well were rinsed once in 1 mL of unbuffered media. 675 µL of unbuffered media was then added to each well, and the plate was incubated for an hour in the absence of additional $CO_2$. Plates were subsequently placed into the calibrated seahorse XF24 flux analyzer for bioenergetic analysis. An equivalent number of cells per well are plated using a cell counter. Further normalization is achieved by taking baseline measurements of OCR on a well-by-well basis, and the increase observed is a comparison to the same well prior to treatment. Thus each well serves as its own control.

Figure 2:
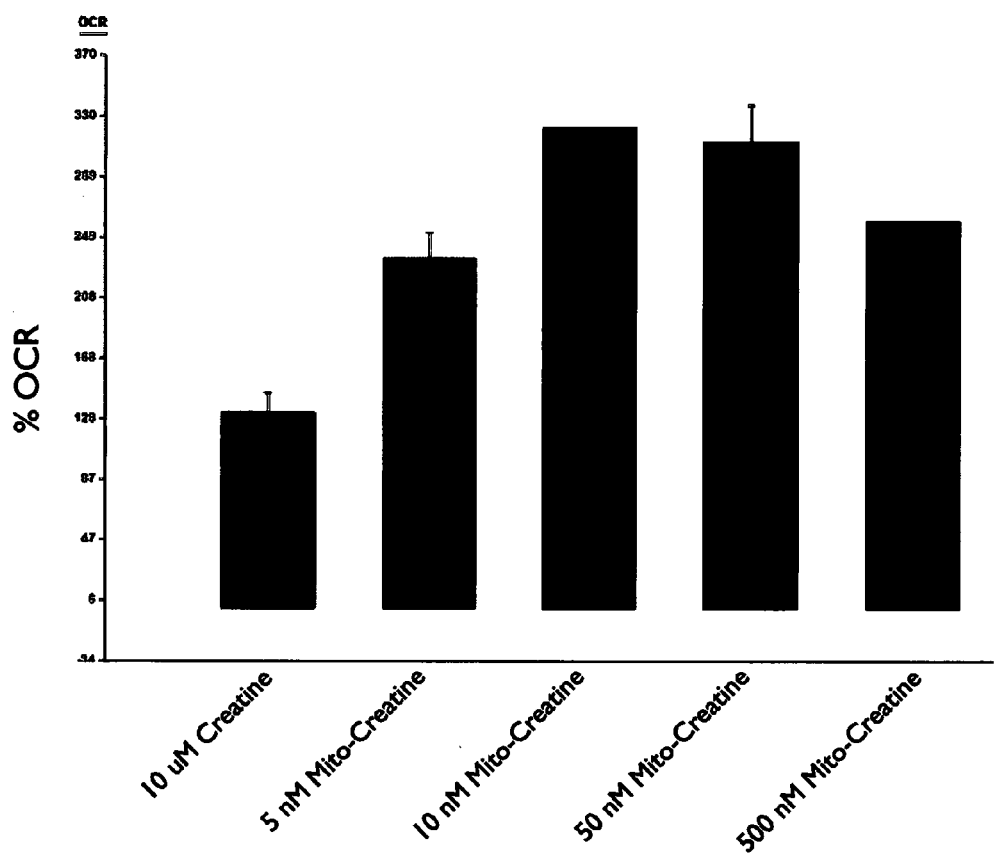
FIG. 2 depicts a bar graph plotting the percent increase in oxygen consumption rate (% OCR) upon addition of 10 µM unmodified creatine and compound 1 ("Mito-Creatine") at 5 nM, 10 nM, 50 nM, and 500 nM concentrations. Compound 1 at increasing concentrations from 5 nM to 500 nM caused a significant increase in oxygen consumption rate within thirty minutes of treatment as compared to unmodified creatine.

The results of the assay for the compound 1 ("Mito-Creatine") at 5 nM, 10 nM, 50 nM, and 500 nM concentrations are shown in FIG. 2 as a percent change from the untreated control. For comparison, the results obtained for compound 1 are compared with the percent increase in oxygen consumption rate measured upon addition of 10 µM creatine. Compound 1 at increasing concentrations from 5 nM to 500 nM caused a significant increase in oxygen consumption rate within thirty minutes of treatment compared to unmodified creatine.

Figure 3:
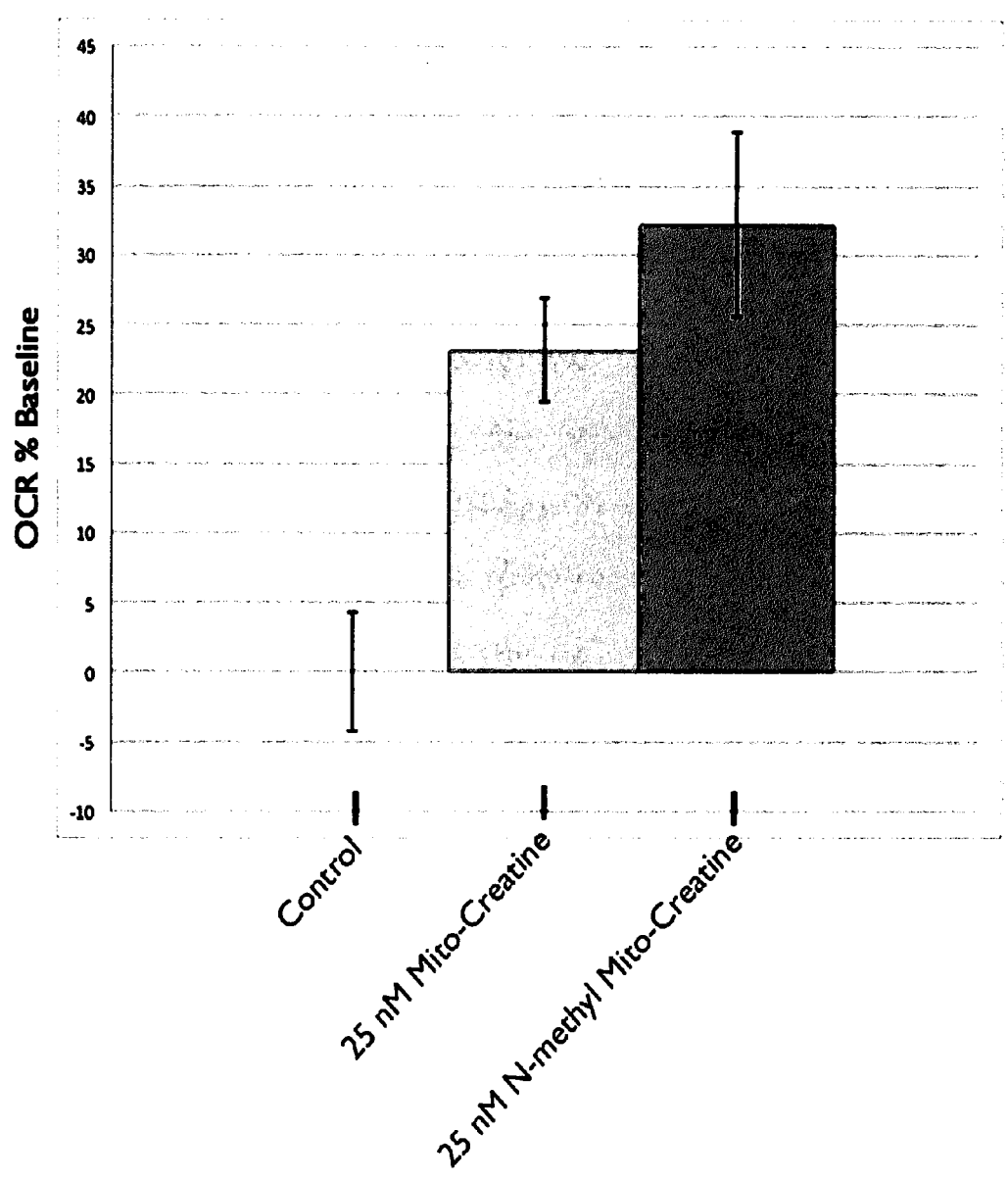
FIG. 3 depicts a bar graph plotting the percent increase in oxygen consumption rate (% OCR) upon addition of 25 nM of compound 1 ("Mito-Creatine") and compound 2 ("N-Methyl Mito-Creatine"). The increase in oxygen consumption rate is plotted as a percent increase in the oxygen consumption as compared to the oxygen consumption rate measured upon addition of 10 µM creatine

Using the same procedure, the oxygen consumption rate for compound 1 ("Mito-Creatine") and the compound of example 2 ("N-Methyl Mito-Creatine") at a concentration of 25 nM were determined. The results obtained for both compounds were plotted in FIG. 3 as percent increase in the oxygen consumption relative to the oxygen consumption rate measured upon addition of 10 µM creatine.

Using the same procedure, the oxygen consumption rate (OCR) for additional compounds were measure in HepG2 human liver carcinoma cells. Compounds were added in concentrations ranging from 0.25 nM to 200 nM. All compounds demonstrated an increase of oxygen consumption rate as shown in Table 3 as expressed as a percentage increase over control (where control is 100 at indicated concentrations.

TABLE 3

| Examples | Concentration (nM) | OCR |
|---|---|---|
| 1 | 10 | 124 |
| 2 | 10 | 106 |
| 5 | 10 | 117.9 |
| 6 | 0.25 | 121 |
| 7 | 20 | 112 |
| 8 | 2.5 | 115.7 |
| 9 | 2.5 | 121.9 |

Example 3

Analysis of Complex I (CI) Activity

The effect of creatine compounds of interest on Complex I (CI) activity in cells was used to determine the ability of the compounds to alter mitochondrial respiration.

Complex I activity was determined using a CI microplate assay (MS 141) from MitoSciences (Eugene, Oreg.) according to the manufacturer's protocol. Fibroblasts were plated in T75 flasks. 24 hours after plating, the cells were treated with various concentrations of compound of example 1 in media for 30 min. The cells were then lysed, and the mitochondria were isolated using reagents provided in the CI assay kit according to the manufacturer's protocol. After determination of the protein concentrations, 20 µg of the purified mitochondria in a total volume of 200 µl was added in quadruplicate to the 96-well microplate and the CI enzyme was immunocaptured within the wells. CI activity was measured colorimetrically with a PHERAstar FS (BMG LABTECH Inc, Cary, N.C., USA) as a change in the absorbance following the oxidation of NADH to NAD+ and the simultaneous reduction of a dye which leads to increased absorbance at 450 nm over time (0-105 min). The average±SD of the quadruplicate values for each time point and treatment group were graphed, and the rate of CI activity was determined by the initial slope (i.e., values in the linear range from 20 to 50 min), expressed as change in optical density per minute.

Figure 4:
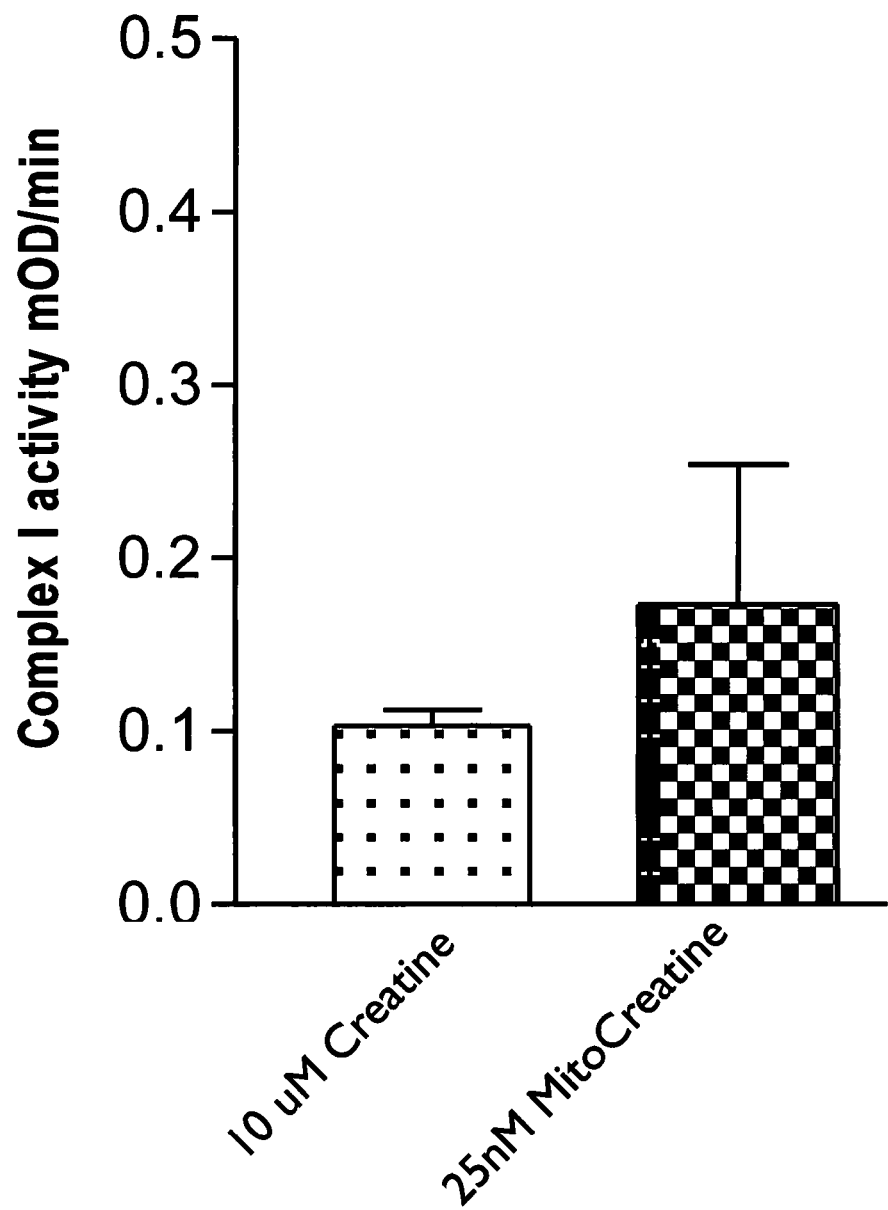
FIG. 4 depicts a bar graph plotting Complex I activity (expressed as change in optical density per minute) upon addition of compound 1 ("MitoCreatine"; 25 nM) and unmodified creatine (10 µM). Incubation with compound 1 induced a significant increase in Complex I activity within thirty minutes as compared to unmodified creatine.

FIG. 4 shows the effect of the compound 1 (25 nM) on Complex I activity within thirty minutes. For comparison, the Complex I activity measured upon addition of 10 µM unmodified creatine is plotted. Incubation with compound 1 induced a significant increase in Complex I activity within thirty minutes.

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A compound of Formula I

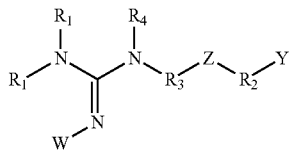

or a pharmaceutically acceptable salt thereof wherein
Z is —C(=O)NR$_5$—;
wherein R$_5$ is hydrogen, alkyl, aryl, or heterocyclic;
Y is a phosphonium group;
each R$_1$ is independently hydrogen, alkyl, or a phosphate group;
R$_2$ is alkyl;
R$_3$ is alkyl, cycloalkyl, alkylcycloalkyl, heterocycloalkyl, or alkylheterocycloalkyl;
R$_4$ is hydrogen, or alkyl;
at each occurrence, an alkyl is optionally substituted with 1-3 substituents independently selected from halo, haloalkyl, hydroxyl, amino, thio, ether, ester, oxo, aldehyde, cycloalkyl, nitrile, urea, amide, carbamate and aryl;
at each occurrence, an aryl is optionally substituted with 1-5 substituents independently selected from halogen, azide, alkyl, haloalkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamide, ketone, aldehyde, ester, heterocyclyl, and CN;
W is hydrogen or alkyl; and with the provisos that Z and Y are not substituted on the same R$_2$ carbon; and that Z and the —NR$_4$— moiety are not substituted on the same R$_3$ carbon.

2. A compound or pharmaceutically acceptable salt of claim 1 wherein
Z is —C(=O)NR$_5$, and R$_5$ is hydrogen or C$_{1-6}$ alkyl;
Y is a phosphonium group;
each R$_1$ is independently hydrogen, alkyl, or a phosphate group;
R$_2$ is alkyl;
R$_3$ is alkyl, cycloalkyl, alkylcycloalkyl, heterocycloalkyl, or alkylheterocycloalkyl; and
R$_4$ is hydrogen, or C$_{1-6}$ alkyl; and W is hydrogen.

3. A compound or pharmaceutically acceptable salt of claim 2 wherein the phosphonium group is selected from —P$^+$(R')$_3$X$^-$, wherein R' is alkyl or aryl; and X$^-$ is an anion.

4. A compound or pharmaceutically acceptable salt of claim 3 wherein R' is phenyl; and X$^-$ is chloride, or trifluoroacetate.

5. A compound or pharmaceutically acceptable salt of claim 2 wherein each R$_1$ is hydrogen, or one R$_1$ is hydrogen, the other R$_1$ is —PO$_3^{2-}$M, wherein M is a cation having one or two position charges.

6. A compound or pharmaceutically acceptable salt of claim 2 wherein R$_2$ is C$_{3-8}$ alkyl.

7. A compound or pharmaceutically acceptable salt of claim 2 wherein R$_3$ is C$_{1-8}$ alkyl or R$_3$ is C$_{1-6}$ alkylheterocycloalkyl wherein heterocycloalkyl is a cyclic ring of 3-10 atoms having at least one hetero atom selected from non-peroxide oxygen, or nitrogen.

8. A compound or pharmaceutically acceptable salt of claim 2 wherein R$_4$ is hydrogen or C$_{1-4}$ alklyl.

9. A compound or pharmaceutically acceptable salt of claim 8 wherein R$_4$ is methyl.

10. A compound or pharmaceutically acceptable salt of claim 8 wherein
Z is —C(=O)NH—,
Y is —P$^+$(Phenyl)$_3$X$^-$, wherein X$^-$ is chloride, or trifluoroacetate;
R$_1$ is hydrogen;
R$_2$ is C$_{1-8}$ alkyl;
R$_3$ is C$_{1-6}$ alkyl, C$_{1-6}$ alkylcycloalkyl wherein cycloalkyl comprising 3-6 carbon atoms, or C$_{1-6}$ alkylheterocycloalkyl wherein heterocycloalkyl is a cyclic ring of 5-6 atoms having a nitrogen atom; and
R$_4$ is methyl.

11. A compound selected from:
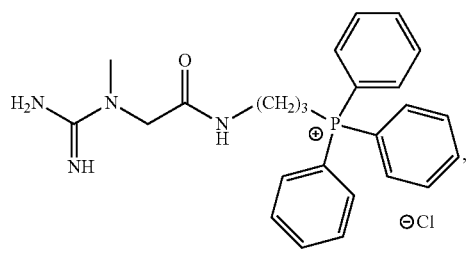
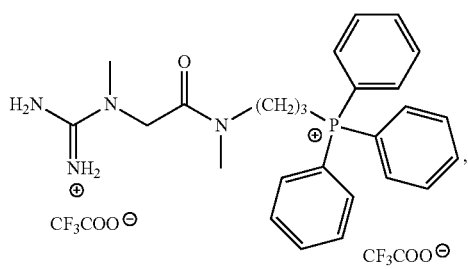
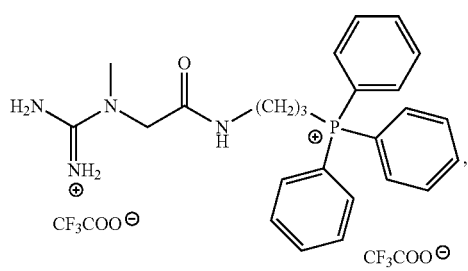
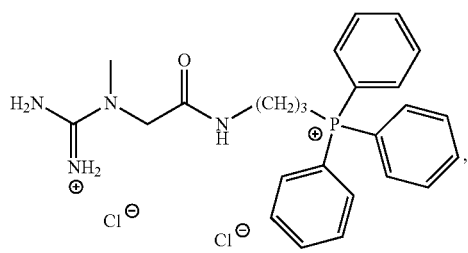
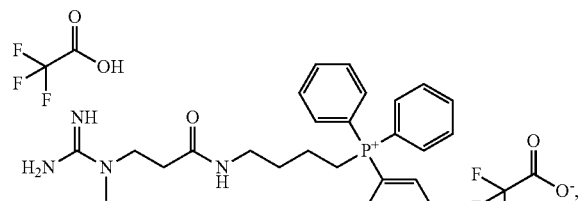
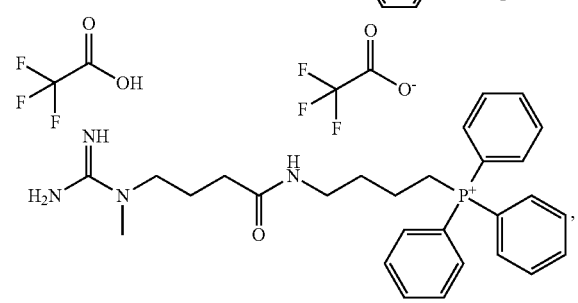
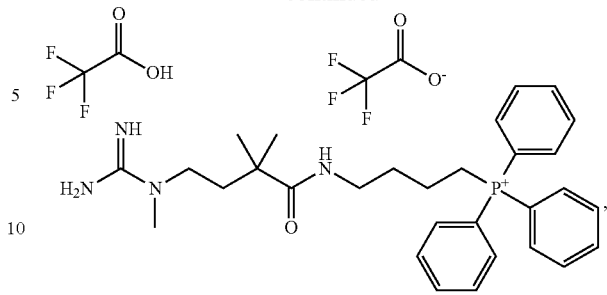
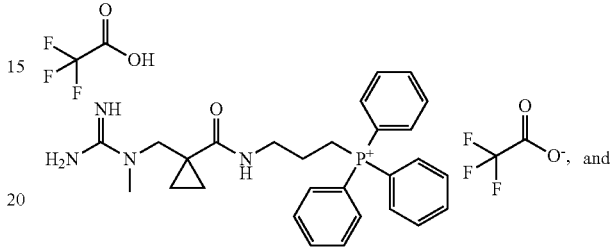
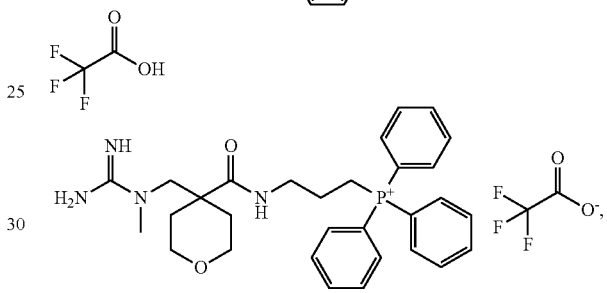
or a pharmaceutically acceptable salt thereof.
12. A compound or a pharmaceutically acceptable salt thereof selected from:
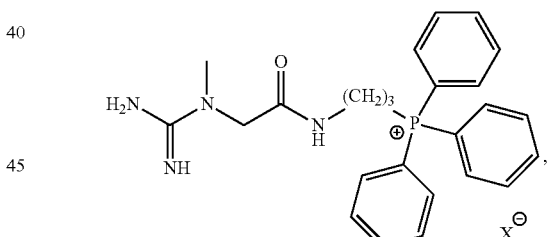
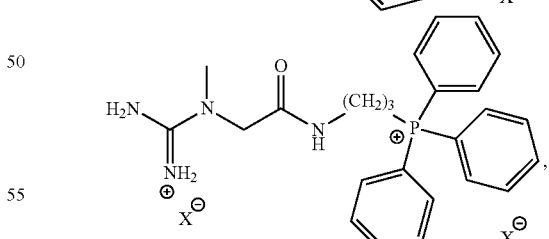
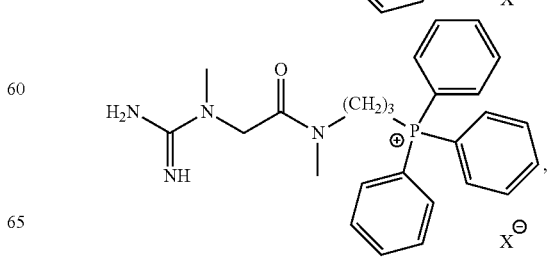

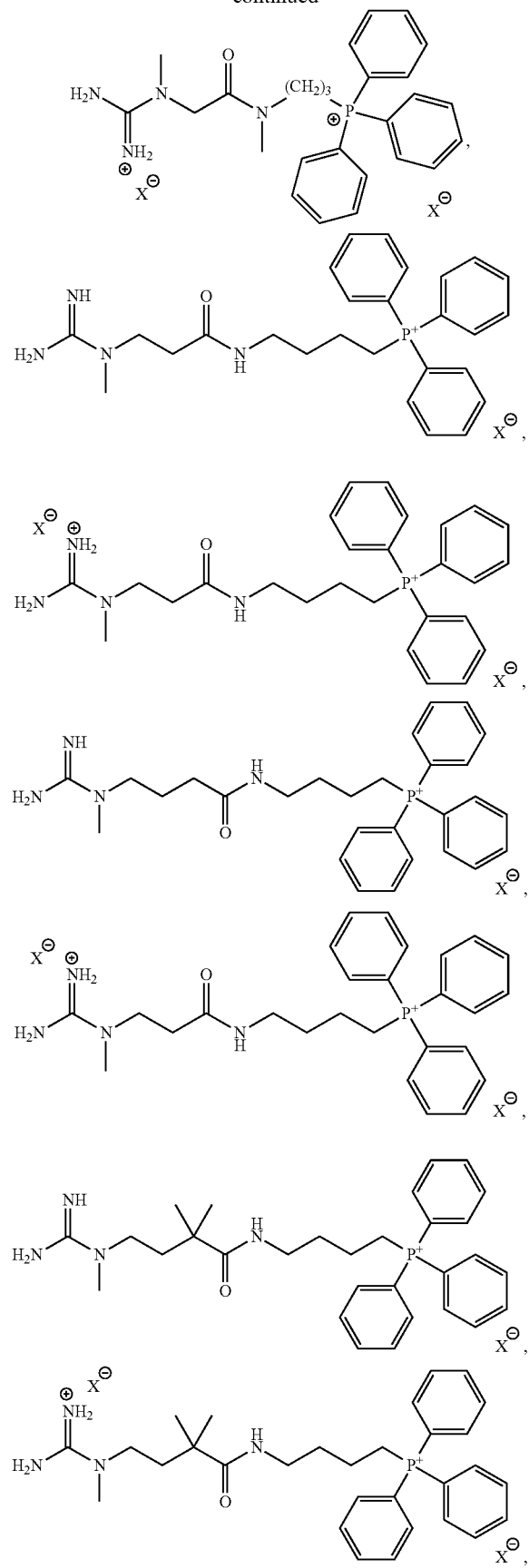
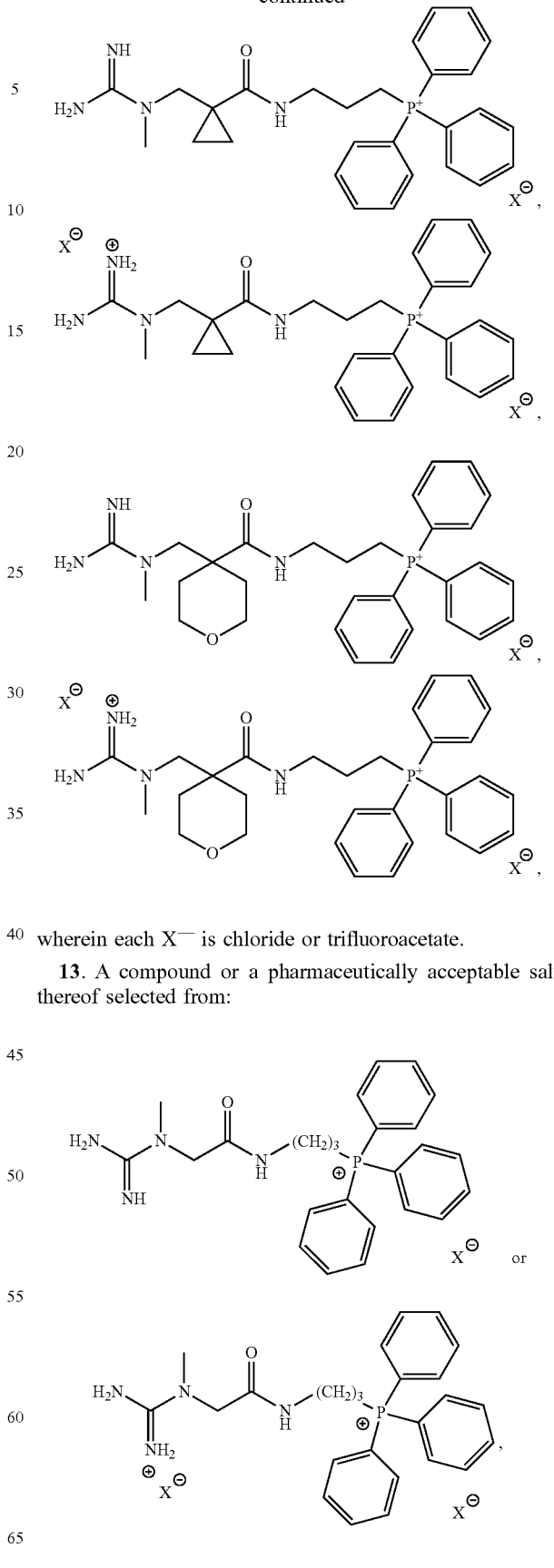
wherein each X⁻ is chloride or trifluoroacetate.
13. A compound or a pharmaceutically acceptable salt thereof selected from:
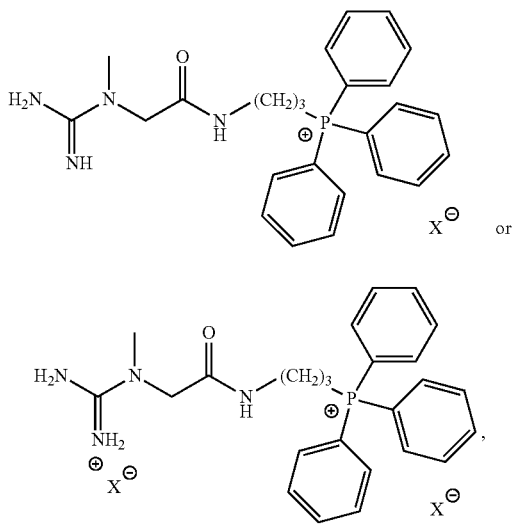
wherein each X⁻ is chloride or trifluoroacetate.

14. A compound or a pharmaceutically acceptable salt thereof selected from:

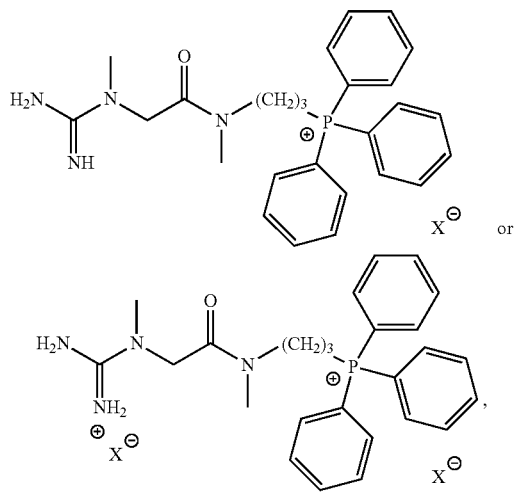

wherein each X⁻ is chloride or trifluoroacetate.

15. A pharmaceutical composition comprising a compound of claim 1.

16. A method of enhancing mitochondrial function in a patient in need thereof, comprising administering the pharmaceutical composition of claim 15 in an amount effective to enhance mitochondrial function in a patient.

17. A method of increasing ATP production in mitochondria of a patient, comprising administering the pharmaceutical composition of claim 15 in an amount effective to increase ATP production in the mitochondria of the patient.

18. A method of treating a mitochondrial myopathy in a patient, comprising administering the pharmaceutical composition of claim 15 in an amount effective to treat one or more symptoms of the mitochondrial myopathy in the patient.

* * * * *